US008980796B2

(12) United States Patent
Cohen et al.

(10) Patent No.: US 8,980,796 B2
(45) Date of Patent: Mar. 17, 2015

(54) CRYSTAL MODIFICATION OF MESOTRIONE

(75) Inventors: Carmen Cohen, Ashdod (IL); Ruben Maidan, Rehovot (IL)

(73) Assignee: Agan Chemical Manufacturers Ltd. (IL)

( * ) Notice: Subject to any disclaimer, the term of this patent is extended or adjusted under 35 U.S.C. 154(b) by 103 days.

(21) Appl. No.: 13/387,197

(22) PCT Filed: Jul. 21, 2010

(86) PCT No.: PCT/IL2010/000580
§ 371 (c)(1),
(2), (4) Date: Mar. 14, 2012

(87) PCT Pub. No.: WO2011/016018
PCT Pub. Date: Feb. 10, 2011

(65) Prior Publication Data
US 2012/0165197 A1    Jun. 28, 2012

Related U.S. Application Data

(60) Provisional application No. 61/273,341, filed on Aug. 3, 2009.

(51) Int. Cl.
*A01N 41/00*    (2006.01)
*A01N 41/10*    (2006.01)
*C07C 317/24*    (2006.01)

(52) U.S. Cl.
CPC ........... *C07C 317/24* (2013.01); *C07C 2101/14* (2013.01); *A01N 41/10* (2013.01); *C07B 2200/13* (2013.01)
USPC ........................................... 504/348; 568/30

(58) Field of Classification Search
CPC ....... A01N 41/00; A01P 13/00; C07C 315/06
USPC ........................................... 504/348; 568/30
See application file for complete search history.

(56) References Cited

U.S. PATENT DOCUMENTS 5,160,530 A    11/1992 Misselbrook et al.
2008/0045751 A1*    2/2008 Wichert et al. ................. 568/30

FOREIGN PATENT DOCUMENTS

EP    0186118 B1    5/1990
WO    WO2006/021743 A1    3/2006
WO    WO2007/083242 A1    7/2007

OTHER PUBLICATIONS

Hahn et al.; Title: Mesotrione—A new herbicide and mode of action; WCU, vol. 12, Jun. 2002.*
Dr. Wamser; Title: Chem 334-Fall 1999, Organic chemistry I; Portland State University Chem 334, Chapter 8 notes, 1999.*
Braga, Dario and Grepioni, Fabrizia, "Making crystals from crystals: a green route to crystal engineering and polymorphism", Chem. Commun. (2005) 3635-3645.
Braga, Dario and Grepioni, Fabrizia, "Chapter 8: Polymorphism, Crystal Transformations and Gas-Solid Reactions", Crystal Design: Structure and Function. vol. 7 (2003) 325-373.
Braga, Dario, et al., "Crystal Polymorphism and multiple crystal forms", Struct Bond (2009) 132, 25-50.
Brittain, H.G., "Preparation and Identification of Polymorphs and Solvatomorph", Preformulation in Solid Dosage Form Development, 185-228 (5th ed., M.C. Adeyeye et al., eds., 2008).
Caira, Mino, "Crystalline polymorphism of Organic Compounds", Topics in Current Chemistry, vol. 198, (1998) 163-208.
Desikan, Sridhar, et al., "Process Development Challenges to Accommodate A Late-Appearing Stable Polymorph: A Case Study on the Polymorphism and Crystallization of a Fast-Track Drug Development Compound", Org. Process Res. & Dev. (2005) 9, 933-942.
Guillory, J. Keith, "Generation of polymorphs, hydrates, solvates, and amorphous solids", Polymorphism in Pharmaceutical Solids, (H.G. Brittain ed., 1999).
Laird, Trevor, "Polymorphism—Still Unpredictable?", Organic Process Research & Development (2010) 14, 1 (Editorial), 1 page.
Morissette, Sherry L., et al., "High-throughput crystallization: polymorphs, salts, co-crystals and solvates of pharmaceutical solids", Advanced Drug Delivery Reviews, 56 (2004) 275-300.
Nangia, Ashwini and Desiraju, Gautam R., "Pseudopolymorphism: occurrences of hydrogen bonding organic solvents in molecular crystals", Chem. Commun. (1999) 605-606.
Roy, Saikat and Matzger, Adam J., "Unmasking a Third Polymorph of a Benchmark Crystal-Structure-Prediction Compound", Angewandte Chemie, Int. Ed. (2009) 48, 8505-8508.
Van Tonder, Elsa C. et al., "Preparation and Physicochemical Characterization of 5 Niclosamide Solvates and 1 Hemisolvate", AAPS PharmSciTech. (2004) 5 (1), 1-10.
Vippagunta, Sudha R. et al., "Crystalline solids", Advanced Drug Delivery Reviews, 48 (2001) 3-26.
International Search Report and Written Opinion for PCT/IL2010/000580 mailed Oct. 26, 2010, 10 pages.
Cabri, Walter, et al., "Polymorphisms and Patent, Market, and Legal Battles: Cefdinir Case Study", Organix Process Research & Development, 2007, 11, 64-72.
Communiction pursuant to Rule 114(2) EPC. Observations by third party concerning EP 10743249.4, dated Nov. 21, 2012, 6 pages.
Papathoma, Sofia, "Patenting Polymorphs at the European Patent Office", presentation Barcelona, Spain, Jun. 19-21, 2006, 1-14.
Brittain et al.; "Effects of pharmaceutical processing on drug polymorphs and solvates"; In H.G. Brittain (ed.) Polymorphism in Pharmaceutical Solids; Marcel Dekker, Inc.; New York; 1999; pp. 331-361.
Gu et al.; "Polymorph Screening: Influence of Solvents on the Rate of Solvent-Mediated Polymorphic Transformation"; Journal of Pharmaceutical Sciences; 2001; 90(11) pp. 1878-1890.
Haleblian et al.; "Pharmaceutical Applications of Polymorphism"; Journal of Pharmaceutical Sciences; Aug. 1969; 58(8); pp. 911-929.
Jain et al.; Polymorphism in Pharmacy; Indian Drugs; 1986; 23(6); pp. 315-329.
Liebenberg; "Crystal Polymorphism and its Occurance Among Active Pharmaceutical Ingredients in South Africa"; North-West University; 2005; 29 pages.

(Continued)

*Primary Examiner* — Richard Schnizer
*Assistant Examiner* — Yanzhi Zhang
(74) *Attorney, Agent, or Firm* — Cantor Colburn LLP

(57) ABSTRACT

The invention relates to a crystalline polymorph Form 3 of 2-[4-(methylsulfonyl)-2-nitrobenzoyl]-1,3-cyclohex-anedione. A process for its preparation, use thereof for the control of weeds, and an herbicidal composition comprising thereof are also disclosed.

18 Claims, 9 Drawing Sheets

(56) References Cited

OTHER PUBLICATIONS

Figure 1:
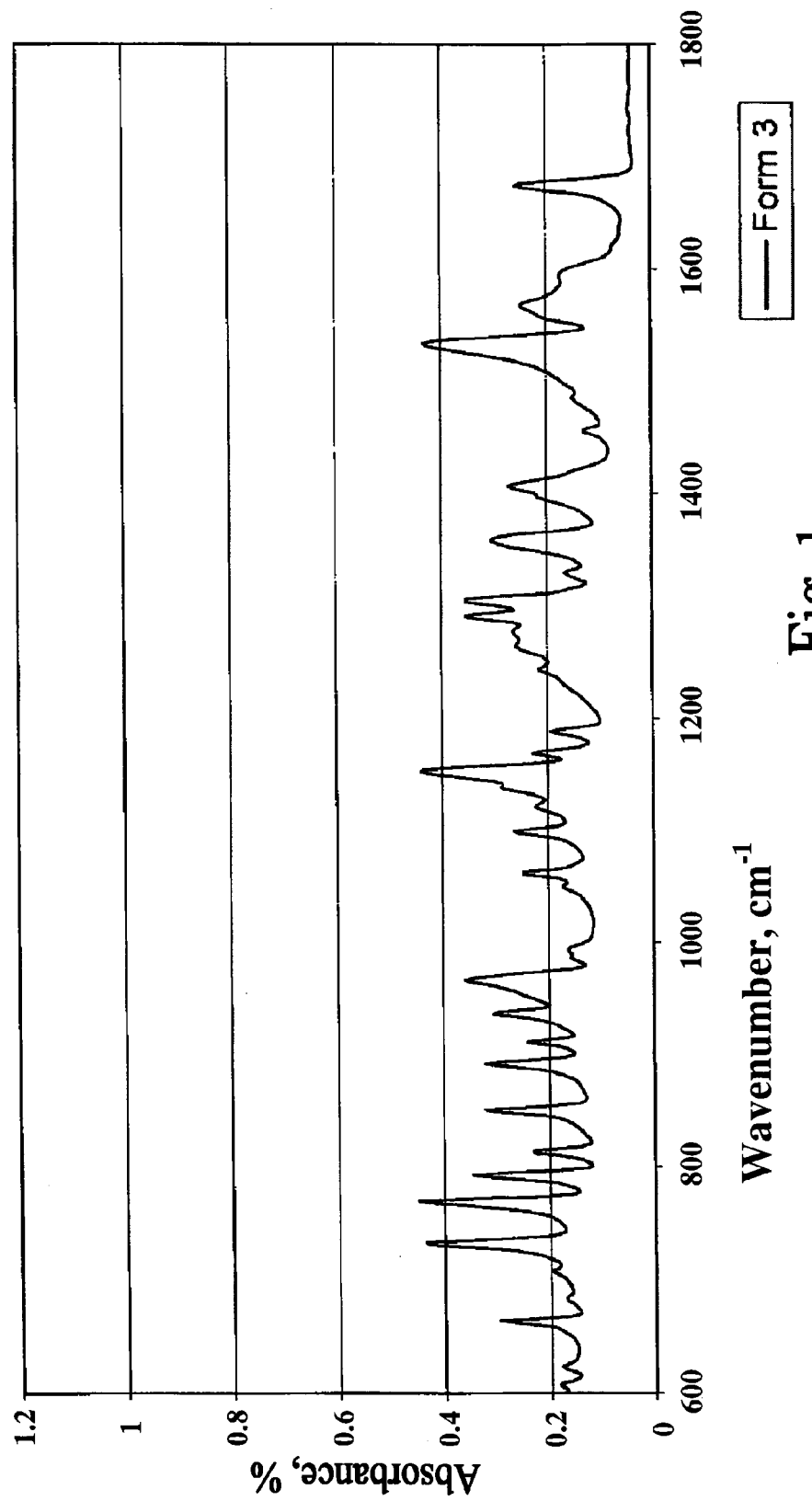

Newman et al.; "Solid-state analysis of the active pharmaceutical ingredient in drug products"; Drug Discovery Today; vol. 8; No. 19; Oct. 2003; pp. 898-905.

O'Connor et al.; "Powders"; Remington: Practice of the Science and Pharmacy; 19th Ed.; Chapter 91; Mack Publishing, Easton, PA; 1995; pp. 1598-1614.

Radebaugh et al.; "Preformulation"; Remington: Practice of the Science and Pharmacy; 19th Ed.; Chapter 83; Mack Publishing, Easton, PA; 1995; pp. 1447-1462.

Rustichelli et al.; "Solid-state study of polymorphic drugs: carbamazenpine"; Journal of Pharmaceutical and Biomedical Analysis; 2000; 23; pp. 41-54.

Schott; "Colloidal Dispersions"; Remington: Practice of the Science and Pharmacy; 19th Ed.; Chapter 20; Mack Publishing, Easton, PA; 1995; pp. 252-277.

Stahly; "Diversity in Single- and Multiple-Component Crystals. The Search for and Prevalence of Polymorphs and Cocrystals"; Crystal Growth & Design; 2007; 7(6); pp. 1007-1026.

Anderton; "A Valuable Technique for Polymorph Screening": American Pharmaceutical Review; Mar./Apr. 2007; pp. 34-40.

Lee et al.; "Crystal Polymorphism in Chemical Process Development"; Annu. Rev. Chem. Biomol. Eng.; 2011; 2; pp. 259-280.

* cited by examiner

CRYSTAL MODIFICATION OF MESOTRIONE

FIELD OF THE INVENTION

The invention relates to a polymorphic form of Mesotrione, methods for its preparation and uses thereof.

BACKGROUND OF THE INVENTION

Mesotrione (2-[4-(methylsulfonyl)-2-nitrobenzoyl]-1,3-cyclohexanedione) is useful as selective herbicide and is widely used for pre and post emergent control of broad leaved weeds in maize.

Mesotrione

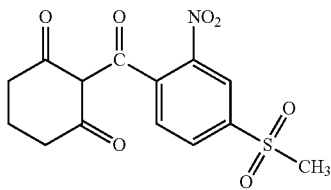 [SMILES: CS(=O)(=O)c1ccc(C(=O)C2C(=O)CCCC2=O)c([N+](=O)[O-])c1]

Its basic synthesis is described in EP 186118.

International Publication Nos. WO2006/021743 (PCT/GB2005/003069) and WO2007/083242 (PCT/IB2007/000198) describe the existence of two crystal modifications of Mesotrione, Form 1 and Form 2.

Mesotrione exists in two polymorphic forms: the thermodynamically stable form, referred to as Form 1; and the metastable form, referred to as Form 2. Form 2 is thermodynamically unstable and would gradually convert to Form 1, consequently any formulation prepared therefrom can lead to instability problems during storage, or it can result in difficulties during the application of the product in the field (WO 2007/083242; WO 2006/021743).

Form 1 is currently the form used in preparing agrochemically acceptable formulations, but during the manufacturing process, Form 2 is readily made when mesotrione is recrystallized in aqueous solution. Due to Form 2 being very fine, it is difficult to filter and production time is lost while trying to remove it from the system. If the Form 2 material obtained during recrystallization cannot be converted to Form 1, then it must be disposed of, resulting in lost revenue and inefficient production processes (WO 2007/083242; WO 2006/021743).

WO 2007/083242 and WO 2006/021743 disclose a process for selectively controlling the crystallization of thermodynamically stable Form 1 or kinetically stable Form 2 polymorphs of mesotrione from an aqueous mesotrione solution.

It will be advantageous to have new polymorphic forms having improved properties such as improved physical, and/or chemical and/or biological and/or phytotoxic properties.

Herbicides are the most widely recognized cause of phytotoxicity. Phytotoxicity is an injury to plants caused by toxic substances.

Improvements in weed control options such as improved selectivity and consequently improved in crop yield are continuously in demand.

Thus, there is a widely recognized need and it will be highly advantages to have an herbicidal compound having reduced phytotoxicity and therefore improved selectivity as compared for example to other form of the compound, as described in the invention.

SUMMARY OF THE INVENTION

The invention relates to a crystalline polymorph Form 3 of 2-[4-(methylsulfonyl)-2-nitrobenzoyl]-1,3-cyclohexanedione (mesotrione) which exhibits at least one of the following properties:

(a) an X-ray powder diffraction pattern having a characteristic peak expressed in 2θ (±0.20°2θ) at 8.0, said peak is characterized by having the highest intensity;

(b) an infrared (IR) absorption spectrum having at least one characteristic peak selected from the following values expressed as $cm^{-1}$ (±1 $cm^{-1}$) at 732, 770, 793, 891, 967, 1121, 1152, 1291, 1304, and 2952;

(c) $^{13}C$ solid state NMR having at least one of the following characteristics:

(i) $^{13}C$ solid state NMR chemical shifts, with reference to a value of 176.03 ppm for the carbonyl peak of glycine, having three peaks in the range 191 to 197 ppm (±0.1 ppm);

(ii) $^{13}C$ solid state NMR, expressed as the difference between the smallest value methylene carbon chemical shift peak and the other chemical shift values, having three peaks in the range 171.4 to 177.4 ppm (±0.1 ppm).

The invention further relates to a crystalline polymorph Form 3 of 2-[4-(methylsulfonyl)-2-nitrobenzoyl]-1,3-cyclohexanedione (mesotrione) which exhibits at least one of the following properties:

(a) an X-ray powder diffraction pattern having a characteristic peak expressed in 2θ (±0.20°2θ) at 8.0, said peak is characterized by having the highest intensity;

(b) an infrared (IR) absorption spectrum having at least one characteristic peak selected from the following values expressed as $cm^{-1}$ (±1 $cm^{-1}$) at 732, 770, 793, 891, 967, 1121, 1152, 1291, 1304, and 2952;

(c) $^{13}C$ solid state NMR having at least one of the following characteristics:

(i) $^{13}C$ solid state NMR chemical shifts, with reference to a value of 176.03 ppm for the carbonyl peak of glycine, having peaks in the range 191 to 197 ppm (±0.1 ppm), comprising at least two peaks selected from the following values 196.1, 192.6, and 192.0 ppm (±0.1 ppm);

(ii) $^{13}C$ solid state NMR, expressed as the difference between the smallest value methylene carbon chemical shift peak and the other chemical shift values, having three peaks in the range 171.4 to 177.4 ppm (±0.1 ppm), comprising at least two peaks selected from the following values 176.5, 173.0, and 172.4 ppm (±0.1 ppm).

The invention additionally relates to crystalline Form 3 of mesotrione characterized by the following solid-state $^{13}C$ nuclear magnetic resonance spectrum wherein chemical shift is expressed in ppm (±0.1 ppm) measured with a 5.0 kHz spin-rate on a Bruker DMX-500 spectrometer, with reference to a value of 176.03 ppm for the carbonyl peak of glycine

| Assignment | Chemical Shift |
|---|---|
| C=O, C=C(OH) | 196.1 |
| C=O, C=C(OH) | 192.6 |
| C=O, C=C(OH) | 192.0 |
| aromatic quaternary carbon | 145.9 |
| aromatic quaternary carbon | 142.4 |
| aromatic quaternary carbon | 140.2 |

-continued

| Assignment | Chemical Shift |
|---|---|
| aromatic methine carbon | 132.1 |
| aromatic methine carbon | 130.3 |
| aromatic methine carbon | 119.9 |
| olefinic carbon alpha to carbonyl | 113.1 |
| methyl carbon | 42.0 |
| methylene carbon | 36.1 |
| methylene carbon | 30.9 |
| methylene carbon | 19.6 |

Further, the invention relates to crystalline Form 3 of mesotrione characterized by the following relative chemical shift values compared to the smallest value methylene carbon chemical shift signal measured in a solid-state $^{13}$C nuclear magnetic resonance spectrum wherein chemical shift is expressed in ppm (±0.1 ppm) measured with a 5.0 kHz spin-rate on a Bruker DMX-500 spectrometer:

| Assignment | Chemical Shift |
|---|---|
| C═O, C═C(OH) | 176.5 |
| C═O, C═C(OH) | 173.0 |
| C═O, C═C(OH) | 172.4 |
| aromatic quaternary carbon | 126.3 |
| aromatic quaternary carbon | 122.8 |
| aromatic quaternary carbon | 120.6 |
| aromatic methine carbon | 112.5 |
| aromatic methine carbon | 110.7 |
| aromatic methine carbon | 100.3 |
| olefinic carbon alpha to carbonyl | 93.5 |
| methyl carbon | 22.4 |
| methylene carbon | 16.5 |
| methylene carbon | 11.3 |
| methylene carbon | 0.0 |

The invention additionally relates to a process for the preparation of a crystalline polymorph Form 3 of 2-[4-(methylsulfonyl)-2-nitrobenzoyl]-1,3-cyclohexanedione as described in the invention, comprising:
- (a) crystallizing Form 3 from an aqueous solution comprising (i) an ammonium salt of 2-[4-(methylsulfonyl)-2-nitrobenzoyl]-1,3-cyclohexanedione and (ii) a polar aprotic solvent selected from dimethylsulfoxide (DMSO), N-methyl-2-pyrrolidone (NMP), dimethylformamide (DMF), and mixtures of said solvents, by acidification of said solution; and
- (b) isolating the resulting precipitate of Form 3.

Moreover the invention relates to a herbicidal composition comprising a crystalline polymorph Form 3 of 2-[4-(methylsulfonyl)-2-nitrobenzoyl]-1,3-cyclohexanedione as described in the invention; and an herbicidally acceptable diluent or carrier.

Further the invention relates to a herbicidal composition as described in the invention for use in weed control.

Still further the invention relates to use of a crystalline polymorph Form 3 as described in the invention for the control of weeds.

Additionally the invention relates to a method for weed control comprising applying to one or both the weeds and their habitat an effective amount the crystalline polymorph Form 3 as described in the invention.

BRIEF DESCRIPTION TO THE DRAWINGS

Figure 2A:
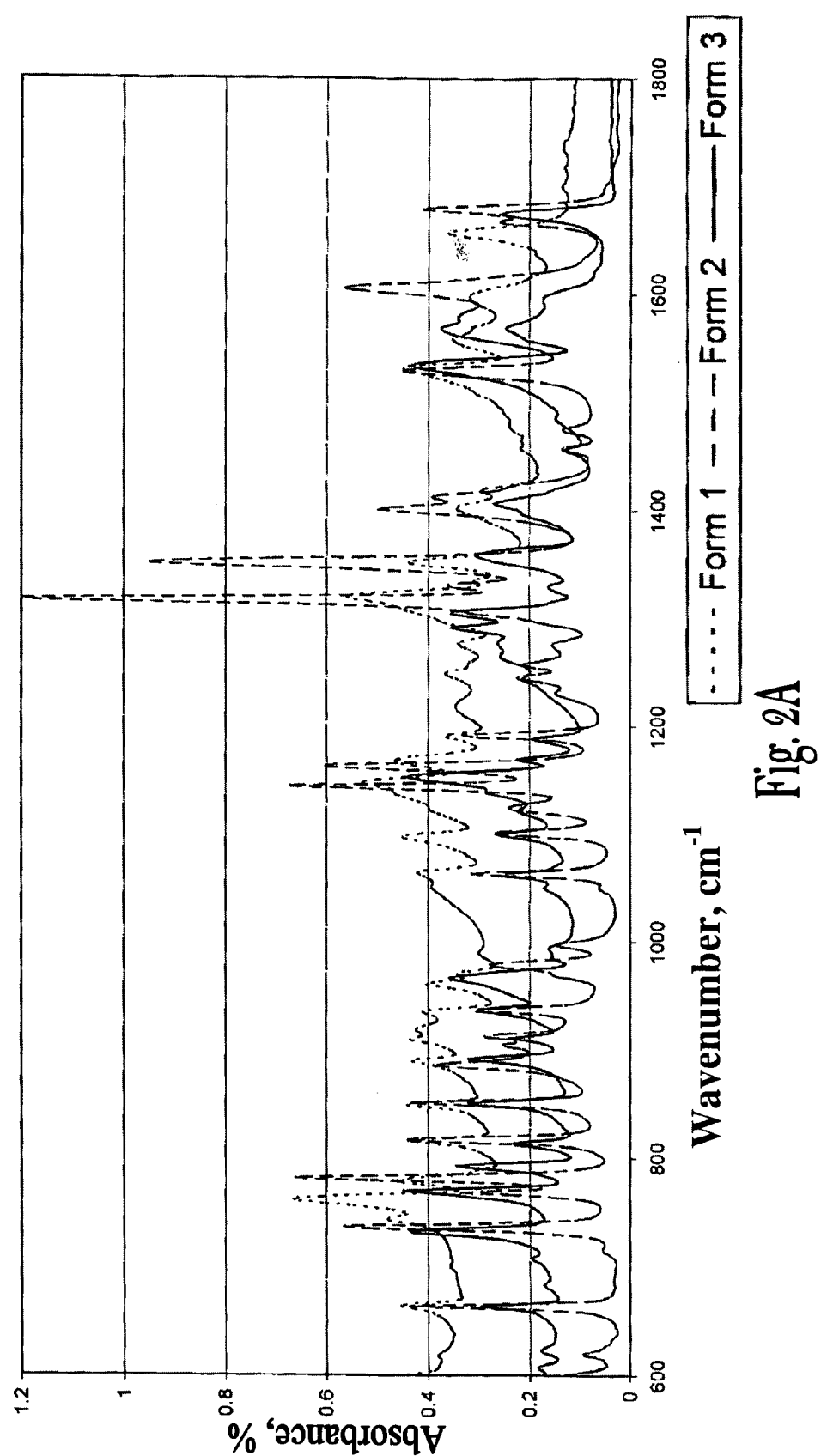
Figure 2B:
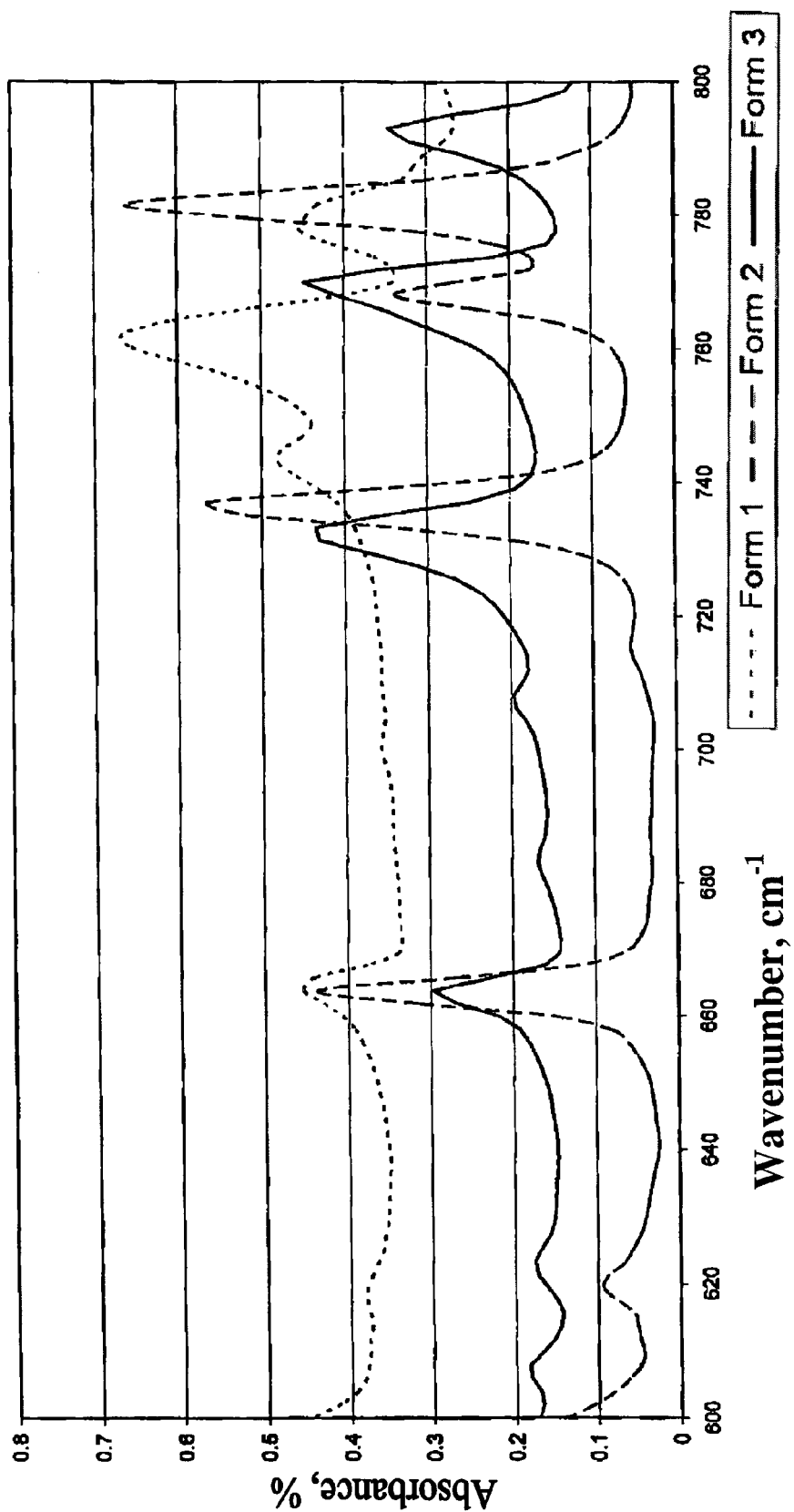
Figure 2C:
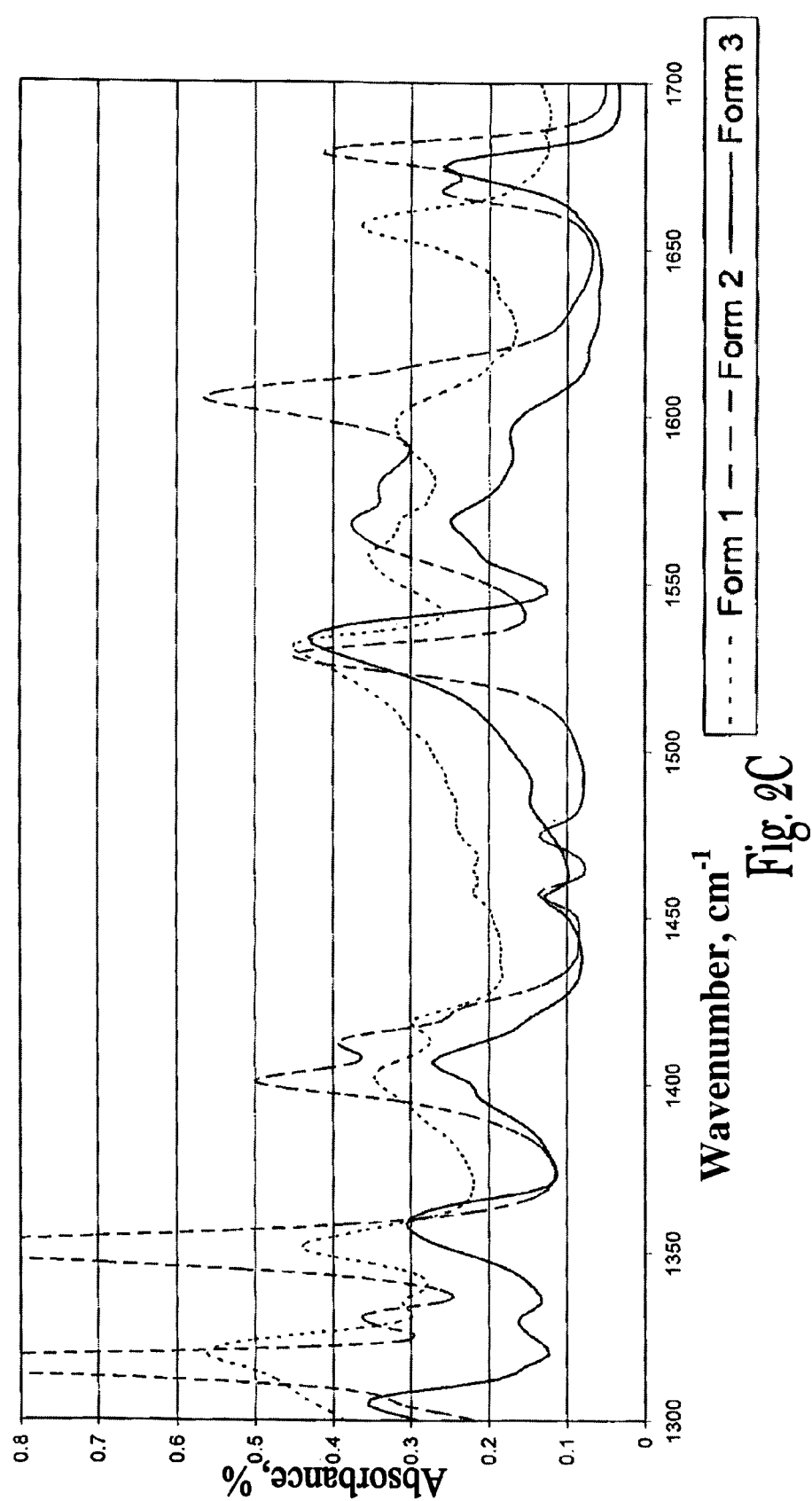
Figure 3:
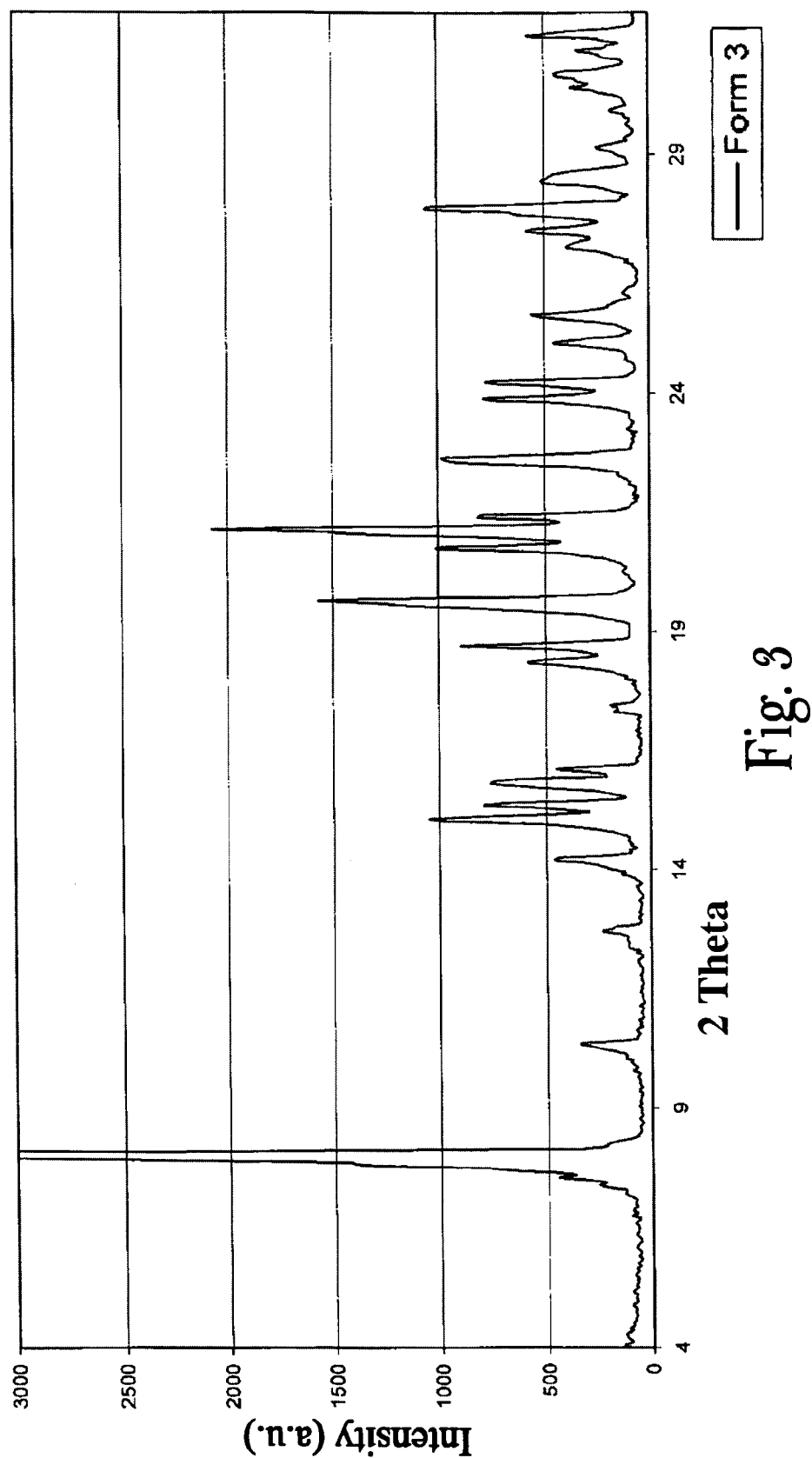
Figure 4:
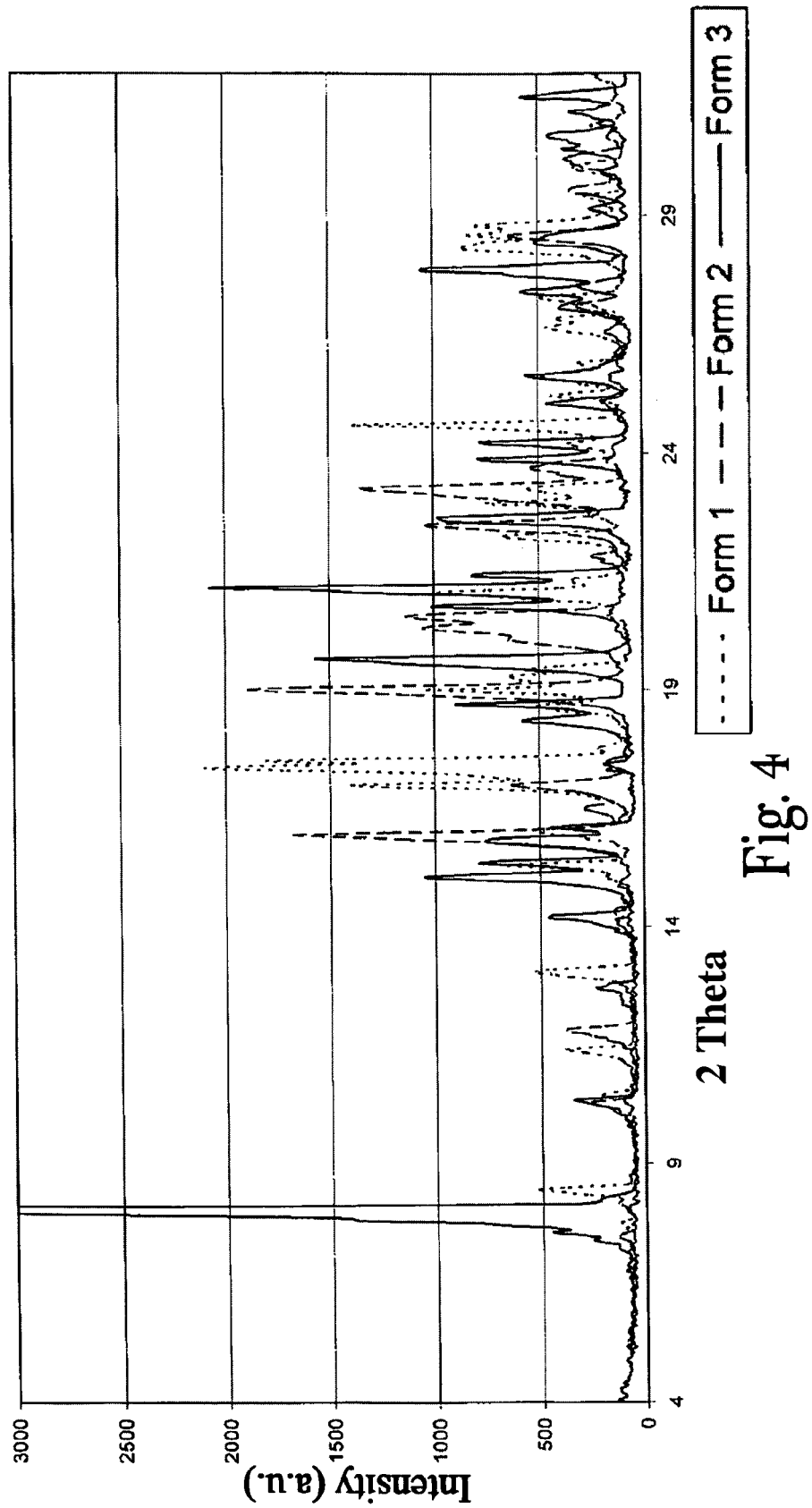
Figure 5:
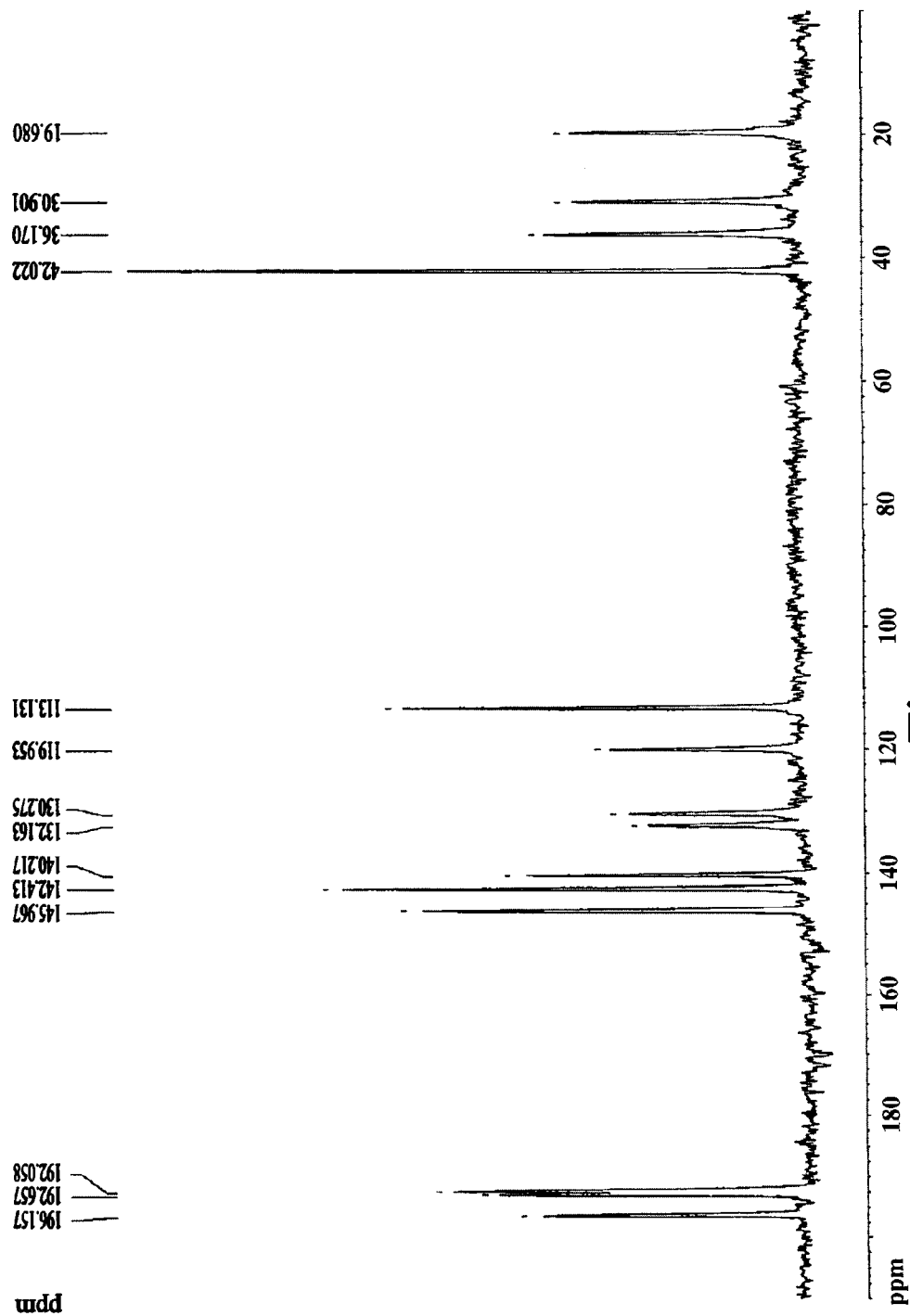
Figure 6:
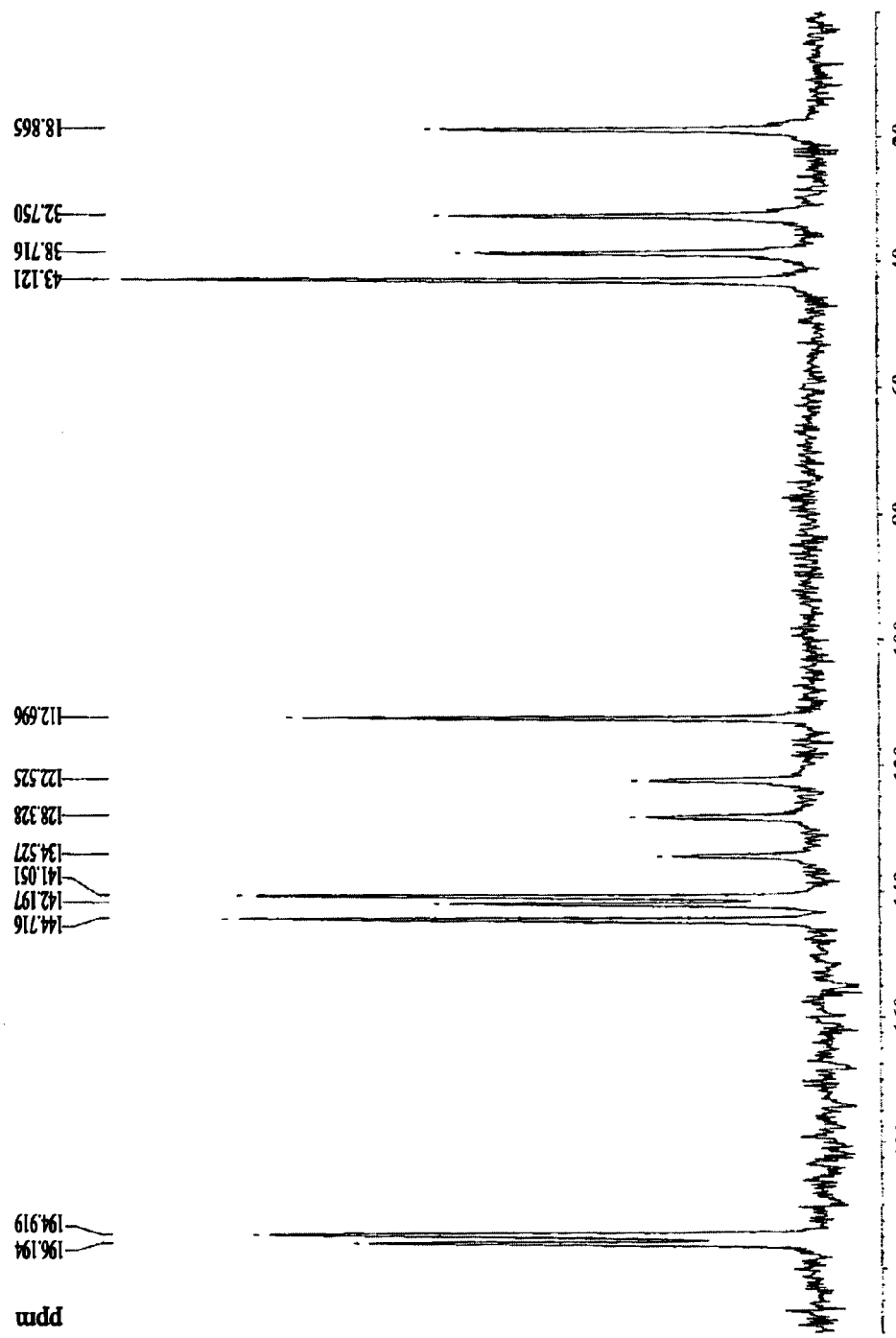
Figure 7:
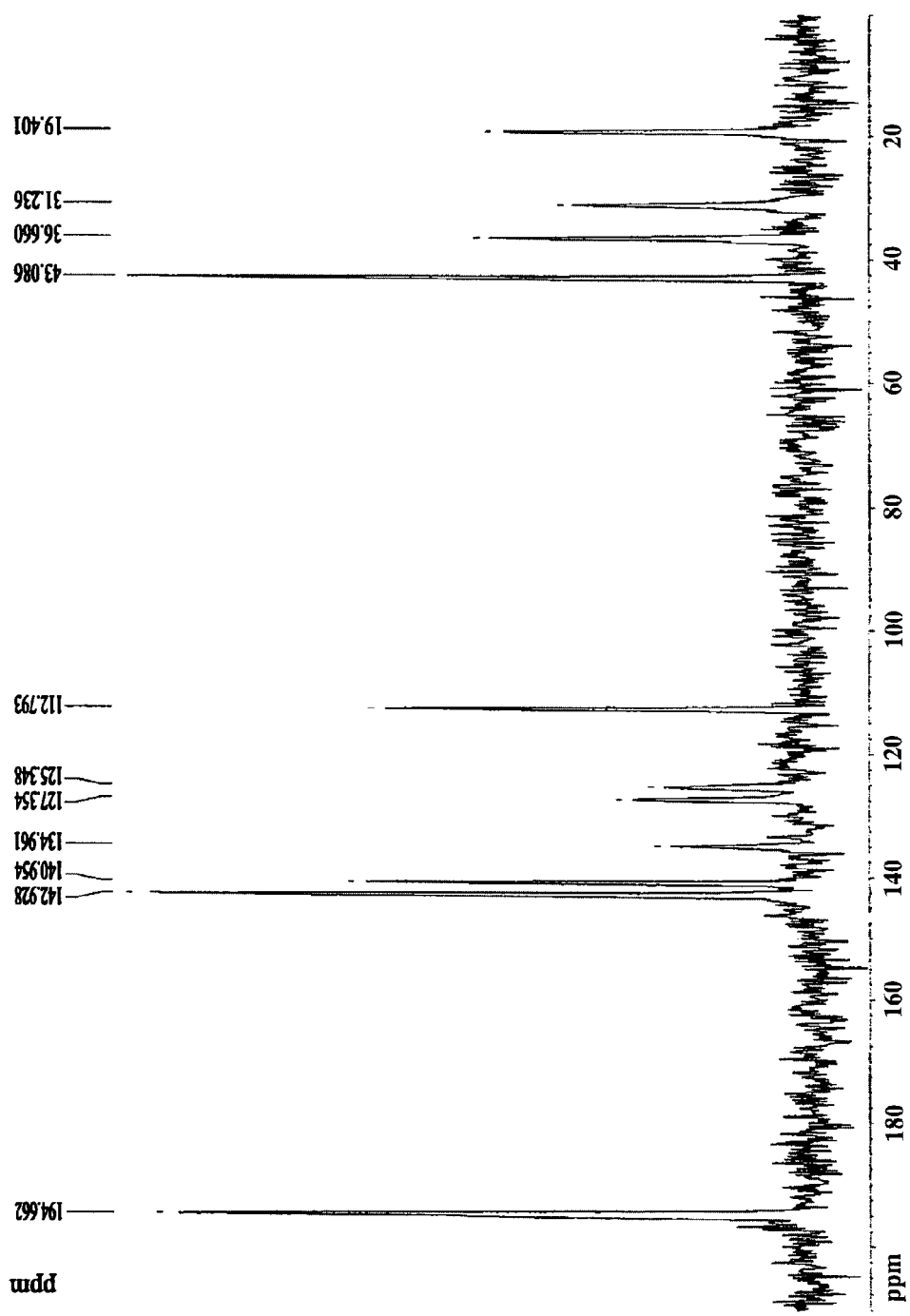

FIG. 1 is a FT-IR spectra of mesotrione Form 3.
FIG. 2*a-c* is an overlaid FT-IR spectra of mesotrione Form 1, 2, and 3. FIG. 2*a* is an overlaid spectra of mesotrione Form 1, 2, and 3 in the range 600-1800 cm$^{-1}$.
FIG. 2*b* is an overlaid spectra of mesotrione Form 1, 2, and 3 in the range 600-800 cm$^{-1}$. FIG. 2*c* is an overlaid spectra of mesotrione Form 1, 2, and 3 in the range 1300-1700 cm$^{-1}$.
FIG. 3 is an X-ray powder diffractogram of mesotrione Form 3.
FIG. 4 is an overlaid X-ray powder diffractogram of mesotrione Form 1, 2 and 3.
FIG. 5 is a C$^{13}$ NMR spectra of mesotrione Form 3.
FIG. 6 is a C$^{13}$ NMR spectra of mesotrione Form 1.
FIG. 7 is a C$^{13}$ NMR spectra of mesotrione Form 2.

DETAILED DESCRIPTION OF THE INVENTION

The inventors of the present application have unexpectedly discovered a new crystalline Form 3 of Mesotrione, designated "Form 3". This crystalline form exhibit a spectral characteristics as depicted by its distinct X-Ray Powder Diffraction (XRD), infrared (IR), and solid state C$^{13}$ NMR (nuclear magnetic resonance) spectra.

Unexpectedly it has been found that new Form 3 of mesotrione exhibits low phytotoxicity when tested on crops as compared to mesotrione form 1.

Such finding is highly advantageous since it provides an improved selective treatment of the herbicide with reduced damage to the crops.

In the following description, XRD, FT-IR, and $^{13}$C NMR data are given for Mesotrione form 3. It should be appreciated that the accuracy of the diffraction angles (2θ (2 Theta) values of peaks) is ±0.2 degree (of 2θ), the accuracy of the FT-IR absorption band peak values is ±1 cm$^{-1}$, and the accuracy of the NMR peak values is ±0.1 ppm.

When referring to the spectra or data presented in graphical form (e.g., XRD, IR, and $^{13}$C NMR spectra), unless otherwise indicated, the term "peak" refers to a peak or other special feature that one skilled in the art would recognize as not attributable to background noise.

Thus, according to one aspect of the invention there is provided a crystalline polymorph Form 3 of 2-[4-(methylsulfonyl)-2-nitrobenzoyl]-1,3-cyclohexanedione (mesotrione) which exhibits at least one of the following properties:
- (a) an X-ray powder diffraction pattern having a characteristic peak expressed in 2θ (±0.20°2θ) at 8.0, said peak is characterized by having the highest intensity;
- (b) an infrared (IR) absorption spectrum having at least one characteristic peak selected from the following values expressed as cm$^{-1}$ (±1 cm$^{-1}$) at 732, 770, 793, 891, 967, 1121, 1152, 1291, 1304, and 2952;
- (c) $^{13}$C solid state NMR having at least one of the following characteristics:
  - (i) $^{13}$C solid state NMR chemical shifts, with reference to a value of 176.03 ppm for the carbonyl peak of glycine, having three peaks in the range 191 to 197 ppm (±0.1 ppm);
  - (ii) $^{13}$C solid state NMR, expressed as the difference between the smallest value methylene carbon chemical shift peak and the other chemical shift values, having three peaks in the range 171.4 to 177.4 ppm (±0.1 ppm).

According to another aspect of the invention there is provided a crystalline polymorph Form 3 of 2-[4-(methylsulfonyl)-2-nitrobenzoyl]-1,3-cyclohexanedione (mesotrione) which exhibits at least one of the following properties:
- (a) an X-ray powder diffraction pattern having a characteristic peak expressed in 2θ (±0.20°2θ) at 8.0, said peak is characterized by having the highest intensity;
- (b) an infrared (IR) absorption spectrum having at least one characteristic peak selected from the following values expressed as cm$^{-1}$ (±1 cm$^{-1}$) at 732, 770, 793, 891, 967, 1121, 1152, 1291, 1304, and 2952;

(c) $^{13}$C solid state NMR having at least one of the following characteristics:

(i) $^{13}$C solid state NMR chemical shifts, with reference to a value of 176.03 ppm for the carbonyl peak of glycine, having peaks in the range 191 to 197 ppm (±0.1 ppm), comprising at least two peaks selected from the following values 196.1, 192.6, and 192.0 ppm (±0.1 ppm);

(ii) $^{13}$C solid state NMR, expressed as the difference between the smallest value methylene carbon chemical shift peak and the other chemical shift values, having three peaks in the range 171.4 to 177.4 ppm (±0.1 ppm), comprising at least two peaks selected from the following values 176.5, 173.0, and 172.4 ppm (±0.1 ppm).

According to a specific embodiment the crystalline polymorph Form 3 of mesotrione exhibits at least the property in item (a).

According to a specific embodiment the crystalline polymorph Form 3 of mesotrione exhibits at least the property in item (b).

According to a specific embodiment the crystalline polymorph Form 3 of mesotrione exhibits at least the property in item (c).

According to a specific embodiment the crystalline polymorph Form 3 of mesotrione exhibits at least two properties selected from item (a), (b), and (c).

According to a specific embodiment the crystalline polymorph Form 3 of mesotrione exhibits two of the properties recited above selected from item (a), (b), and (c) (e.g. items (a) and (b); or items (a) and (c); or items (b) and (c)).

According to a specific embodiment the crystalline polymorph Form 3 of mesotrione exhibits all three of the properties recited above in items (a), (b), and (c).

Referring to item (c), the $^{13}$C solid state NMR have a characteristic selected from item (i) and item (ii). In a specific embodiment the $^{13}$C solid state NMR is characterized by items (i) and (ii). In a specific embodiment the $^{13}$C solid state NMR is characterized by item (i). In a specific embodiment the $^{13}$C solid state NMR is characterized by item (ii).

According to a specific embodiment the $^{13}$C solid state NMR chemical shifts are measured with a 5.0 kHz spin-rate on a Bruker DMX-500 spectrometer.

As used herein by "$^{13}$C solid state NMR chemical shifts, with reference to a value of 176.03 ppm for the carbonyl peak of glycine" is meant that the NMR chemical shifts measurements are calibrated by the 176.03 ppm carbonyl signal of glycine alpha-polymorph as an external spectral reference.

The term "ppm" refers to parts per million.

According to a specific embodiment the three peaks, with reference to a value of 176.03 ppm for the carbonyl peak of glycine, are in the range 191.5 to 196.5 ppm (±0.1 ppm).

According to a more specific embodiment the three peaks, with reference to a value of 176.03 ppm for the carbonyl peak of glycine, are in the range 191.8 to 196.5 ppm (±0.1 ppm). According to even more specific embodiment the three peaks, with reference to a value of 176.03 ppm for the carbonyl peak of glycine, are in the range 191.8 to 196.3 ppm (±0.1 ppm).

According to some embodiments the three peaks, with reference to a value of 176.03 ppm for the carbonyl peak of glycine, have at least one peak selected from 196.1, 192.6, and 192.0 ppm (±0.1 ppm).

In some embodiments the at least one peak value is 196.1 ppm (±0.1 ppm). In some embodiments the at least one peak value is 192.6 ppm (±0.1 ppm). In some embodiments the at least one peak value is 192.0 ppm (±0.1 ppm).

According to some embodiments the $^{13}$C solid state NMR chemical shifts, with reference to a value of 176.03 ppm for the carbonyl peak of glycine, have at least two peak values selected from 196.1, 192.6, and 192.0 ppm (±0.1 ppm).

In some embodiments the at least two peak values are 196.1 and 192.6 ppm (±0.1 ppm). In some embodiments the at least two peak values are 196.1 and 192.0 ppm (±0.1 ppm). In some embodiments the at least two peak values are 192.6 and 192.0 ppm (±0.1 ppm). According to a specific embodiment the $^{13}$C solid state NMR chemical shifts, with reference to a value of 176.03 ppm for the carbonyl peak of glycine, have all three of the values recited above (i.e. three peak values at 196.1, 192.6, and 192.0 ppm (±0.1 ppm)).

Form 3 can be readily distinguished by $^{13}$C solid state NMR by the characteristic peaks in the region 191-197 ppm. In this region Form 3 has 3 characteristic peaks.

In this region Form 1 has two peaks at 196.580 and 195.366 ppm according to the information provided in WO 2006/021743. Form 2 has one peak in this region at 195.275 according to the information provided in WO 2006/021743.

Thus, Form 3 may be also distinguished from Form 1 and 2 by having at least two peak values selected from 196.1, 192.6, and 192.0 ppm.

According to some embodiments the $^{13}$C solid state NMR chemical shifts with reference to a value of 176.03 ppm for the carbonyl peak of glycine further characterized by having at least one additional peak expressed in ppm (±0.1 ppm), selected from the following values at 145.9, 142.4, 140.2, 132.1, 130.3, 119.9, 113.1, 42.0, 36.1, 30.9, and 19.6.

In some embodiments, the $^{13}$C solid state NMR of mesotrione Form 3 is characterized in that it has at least two of these $^{13}$C solid state NMR peak values.

In some embodiments, the $^{13}$C solid state NMR of mesotrione Form 3 is characterized in that it has at least three of these $^{13}$C solid state NMR peak values.

In some embodiments, the $^{13}$C solid state NMR of mesotrione Form 3 is characterized in that it has at least four of these $^{13}$C solid state NMR peak values.

In some embodiments, the $^{13}$C solid state NMR of mesotrione Form 3 is characterized in that it has at least five of these $^{13}$C solid state NMR peak values.

In some embodiments, the $^{13}$C solid state NMR of mesotrione Form 3 is characterized in that it has at least six of these $^{13}$C solid state NMR peak values.

In some embodiments, the $^{13}$C solid state NMR of mesotrione Form 3 is characterized in that it has at least seven of these $^{13}$C solid state NMR peak values.

In some embodiments, the $^{13}$C solid state NMR of mesotrione Form 3 is characterized in that it has at least eight of these $^{13}$C solid state NMR peak values.

In some embodiments, the $^{13}$C solid state NMR of mesotrione Form 3 is characterized in that it has at least nine of these $^{13}$C solid state NMR peak values.

In some embodiments, the $^{13}$C solid state NMR of mesotrione Form 3 is characterized in that it has at least ten of these $^{13}$C solid state NMR peak values.

In some embodiments, the $^{13}$C solid state NMR of mesotrione Form 3 is characterized in that it has all eleven of these $^{13}$C solid state NMR peak values.

According to a specific embodiment $^{13}$C solid state NMR chemical shifts, with reference to a value of 176.03 ppm for the carbonyl peak of glycine, expressed in ppm (±0.1 ppm), have the following peak values:

| Assignment | Chemical Shift |
| --- | --- |
| C=O, C=C(OH) | 196.1 |
| C=O, C=C(OH) | 192.6 |
| C=O, C=C(OH) | 192.0 |
| aromatic quaternary carbon | 145.9 |
| aromatic quaternary carbon | 142.4 |
| aromatic quaternary carbon | 140.2 |
| aromatic methine carbon | 132.1 |
| aromatic methine carbon | 130.3 |
| aromatic methine carbon | 119.9 |
| olefinic carbon alpha to carbonyl | 113.1 |
| methyl carbon | 42.0 |
| methylene carbon | 36.1 |
| methylene carbon | 30.9 |
| methylene carbon | 19.6 |

According to a specific embodiment the three peaks, expressed as the difference between the smallest value methylene carbon chemical shift peak and the other chemical shift values, are in the range 171.9 to 176.9 ppm (±0.1 ppm).

According to a more specific embodiment the three peaks, expressed as the difference between the smallest value methylene carbon chemical shift peak and the other chemical shift values, are in the range 172.2 to 176.9 ppm (±0.1 ppm). According to even more specific embodiment the three peaks, expressed as the difference between the smallest value methylene carbon chemical shift peak and the other chemical shift values, are in the range 172.2 to 176.7 ppm (±0.1 ppm).

According to some embodiments the three peaks, expressed as the difference between the smallest value methylene carbon chemical shift peak and the other chemical shift values, have at least one peak selected from 176.5, 173.0, and 172.4 ppm (±0.1 ppm).

In some embodiments the at least one peak value is 176.5 ppm (±0.1 ppm). In some embodiments the at least one peak value is 173.0 ppm (±0.1 ppm). In some embodiments the at least one peak value is 172.4 ppm (±0.1 ppm).

According to some embodiments the $^{13}$C solid state NMR chemical shifts, expressed as the difference between the smallest value methylene carbon chemical shift peak and the other chemical shift values, have at least two peak values selected from 176.5, 173.0, and 172.4 ppm (±0.1 ppm).

In some embodiments the at least two peak values are 176.5 and 173.0 ppm (±0.1 ppm). In some embodiments the at least two peak values are 176.5 and 172.4 ppm (±0.1 ppm). In some embodiments the at least two peak values are 173.0 and 172.4 ppm (±0.1 ppm). According to a specific embodiment the $^{13}$C solid state NMR chemical shifts, expressed as the difference between the smallest value methylene carbon chemical shift peak and the other chemical shift values, have all three of the values recited above (i.e. three peak values at 176.5, 173.0 and 172.4 ppm (±0.1 ppm)).

According to some embodiments the $^{13}$C solid state NMR expressed as the difference between the smallest value methylene carbon chemical shift peak and the other chemical shift values, is further characterized by having at least one additional chemical shift difference values selected from the following values at 126.3, 122.8, 120.6, 112.5, 110.7, 100.3, 93.5, 22.4, 16.5, 11.3, and 0.0. ppm (±0.1 ppm).

In some embodiments, the $^{13}$C solid state NMR of mesotrione Form 3 is characterized in that it has at least two of these $^{13}$C solid state NMR chemical shift difference values.

In some embodiments, the $^{13}$C solid state NMR of mesotrione Form 3 is characterized in that it has at least three of these $^{13}$C solid state NMR chemical shift difference values.

In some embodiments, the $^{13}$C solid state NMR of mesotrione Form 3 is characterized in that it has at least four of these $^{13}$C solid state NMR chemical shift difference values.

In some embodiments, the $^{13}$C solid state NMR of mesotrione Form 3 is characterized in that it has at least five of these $^{13}$C solid state NMR chemical shift difference values.

In some embodiments, the $^{13}$C solid state NMR of mesotrione Form 3 is characterized in that it has at least six of these $^{13}$C solid state NMR chemical shift difference values.

In some embodiments, the $^{13}$C solid state NMR of mesotrione Form 3 is characterized in that it has at least seven of these $^{13}$C solid state NMR chemical shift difference values.

In some embodiments, the $^{13}$C solid state NMR of mesotrione Form 3 is characterized in that it has at least eight of these $^{13}$C solid state NMR chemical shift difference values.

In some embodiments, the $^{13}$C solid state NMR of mesotrione Form 3 is characterized in that it has at least nine of these $^{13}$C solid state NMR chemical shift difference values.

In some embodiments, the $^{13}$C solid state NMR of mesotrione Form 3 is characterized in that it has at least ten of these $^{13}$C solid state NMR chemical shift difference values.

In some embodiments, the $^{13}$C solid state NMR of mesotrione Form 3 is characterized in that it has all eleven of these $^{13}$C solid state NMR chemical shift difference values.

According to some embodiments the $^{13}$C solid state NMR expressed as the difference between the smallest value methylene carbon chemical shift peak and the other chemical shift values, is characterized by having the following peak difference values, expressed in ppm (±0.1 ppm):

| Assignment | Chemical Shift |
| --- | --- |
| C=O, C=C(OH) | 176.5 |
| C=O, C=C(OH) | 173.0 |
| C=O, C=C(OH) | 172.4 |
| aromatic quaternary carbon | 126.3 |
| aromatic quaternary carbon | 122.8 |
| aromatic quaternary carbon | 120.6 |
| aromatic methine carbon | 112.5 |
| aromatic methine carbon | 110.7 |
| aromatic methine carbon | 100.3 |
| olefinic carbon alpha to carbonyl | 93.5 |
| methyl carbon | 22.4 |
| methylene carbon | 16.5 |
| methylene carbon | 11.3 |
| methylene carbon | 0.0 |

Form 3 can be readily distinguished by X-ray powder diffraction from Form 1 and 2 by having a very strong peak (having the highest intensity) at about 2θ=8.0. Forms 1 and 2 do not exhibit this feature.

According to a specific embodiment the X-ray powder diffraction is recorded using Cu—Kα radiation (λ=1.541 Å).

According to a specific embodiment the X-ray powder diffraction is recorded at room temperature.

As used herein the term "room temperature" refers to a temperature in the range 20-25° C.

Referring to the X-ray powder diffraction data, as used herein by the term "a characteristic peak . . . at 8.0, said peak is characterized by having the highest intensity" means that the peak at 2θ=8.0±0.20 has the largest peak intensity in a given diffractogram.

In some embodiments the ratio between the peak having the highest intensity and the peak having the second highest intensity is above 2. In some embodiments the ratio between the peak having the highest intensity and the peak having the second highest intensity is above 3. In some embodiments the ratio between the peak having the highest intensity and the peak having the second highest intensity is above 4. In some embodiments the ratio between the peak having the highest intensity and the peak having the second highest intensity is above 5.

The ratio between the peak having the highest intensity and the peak having the second highest intensity may be for example in the range 2 to 10; or 2 to 9; or 3 to 8; or 4 to 8; or 5 to 8.

According to some embodiments the X-ray powder diffraction pattern further characterized by having at least one additional peak expressed in 2θ (±0.20°2θ) selected from the following values at 15.0, 19.6, and 27.9.

By "peak expressed in 2θ (±0.20°2θ) selected from the following values at 15.0, 19.6, and 27.9" is meant a peak selected from the following values at 15.0±0.20, 19.6±0.20, and 27.9±0.20°2θ.

According to some embodiments the X-ray powder diffraction pattern further characterized by having at least one additional peak expressed in 2θ (±0.20°2θ) selected from the following values at 12.7 and 18.4.

According to some embodiments the X-ray powder diffraction pattern further characterized by having at least one additional peak expressed in 2θ (±0.20°2θ) selected from the following values at 12.7, 15.0, 18.4, 19.6, and 27.9.

The X-ray powder diffraction pattern may be characterized by having at least one additional peak, at least two additional peaks, at least three additional peaks, at least four additional peaks, at least five additional peaks from the values recited above.

According to some embodiments the X-ray powder diffraction pattern further characterized by having at least one additional peak expressed in 2θ (±0.20°2θ) selected from the following values at 12.7, 15.0, 18.4, 19.6, 20.8, 22.6, 23.9, and 27.4, and 27.9.

The X-ray powder diffraction pattern may be characterized by having at least one additional peak, at least two additional peaks, at least three additional peaks, etc. up to nine additional peaks from the values recited above.

According to another aspect of the invention there is provided a crystalline polymorph Form 3 of 2-[4-(methylsulfonyl)-2-nitrobenzoyl]-1,3-cyclohexanedione (mesotrione) which exhibits at least one of the following properties:
(a) an X-ray powder diffraction pattern having a characteristic peak expressed in 2θ (±0.20°2θ) at 8.0 (very strong);
(b) an infrared (IR) absorption spectrum having at least one characteristic peak selected from the following values expressed as cm$^{-1}$ (±1 cm$^{-1}$) at 732, 770, 793, 891, 967, 1121, 1152, 1291, 1304, and 2952;
(c) $^{13}$C solid state NMR chemical shifts expressed relative to glycine having three peaks in the range 191 to 197 ppm (±0.1 ppm).

In some embodiments the X-ray powder diffraction pattern is characterized by having (i) a peak expressed in 2θ (±0.20°2θ) at 8.0 (very strong); and (ii) at least one peak expressed in 2θ (±0.20°2θ) selected from the following values: 12.7 (weak), 15.0 (medium), 18.4 (medium), 19.6 (strong), 27.9 (medium).

In some embodiments the X-ray powder diffraction pattern is characterized by having (i) a peak expressed in 2θ (±0.20°2θ) at 8.0 (very strong); and (ii) at least one peak expressed in 2θ (±0.20°2θ) selected from the following values: 12.7 (weak), 15.0 (medium), 18.4 (medium), 19.6 (strong), 20.8(medium), 22.6 (medium), 23.9 (medium), and 27.4 (medium), and 27.9 (medium).

The X-ray powder diffraction pattern may be characterized by having at least one additional peak, at least two additional peaks, at least three additional peaks, etc. up to nine additional peaks from the values recited above in item (ii).

The term "relative intensity" as used herein refers to an intensity value derived from a sample X-ray diffraction pattern. The complete ordinate range scale for a diffraction pattern is assigned a value of 100.

Relative intensity is calculated as a ratio of the peak intensity of the peak of interest versus the peak intensity of the largest peak.

A peak having intensity falling between above 25% to 100% on this scale intensity is termed very strong (vs); a peak having intensity falling between above 10% to 25% is termed strong (s); a peak having intensity falling between above 3% to 10% is termed medium (m); a peak having intensity falling between above 1% to 3% is termed weak (w). Additional weaker peaks may be present in typical diffraction patterns.

According to a certain aspect of the invention the X-ray powder diffraction is characterized by the following reflections quoted below as interplanar spacing d or as 2θ values:

| | |
|---|---|
| d = 6.97 Å | 2θ = 12.7 ± 0.20° |
| d = 5.89 Å | 2θ = 15.0 ± 0.20° |
| d = 4.83 Å | 2θ = 18.4 ± 0.20° |
| d = 4.52 Å | 2θ = 19.6 ± 0.20° |
| d = 3.20 Å | 2θ = 27.9 ± 0.20° |

According to a specific embodiment the X-ray powder diffraction is further characterized by at least one of the following reflections quoted below as interplanar spacing d or as 2θ values:

The d values may deviate as much as ±1% of the indicated d values.

In some embodiments, the mesotrione Form 3 is characterized in that it has at least two of these 2θ values or d values.

In some embodiments, the mesotrione Form 3 is characterized in that it has at least three of these 2θ values or d values.

In some embodiments, the mesotrione Form 3 is characterized in that it has at least four of these 2θ values or d values.

In some embodiments, the mesotrione Form 3 is characterized in that it has at least five of these 2θ values or d values.

As used herein the term "at least two of these 2θ values" relates to any combination of at least two 2θ values selected from the above values. Similarly, the term "at least three of these 2θ values" relates to any combination of at least three 2θ values selected from the above values, etc.

In some embodiments mesotrione Form 3 have an X-ray powder diffraction comprising at least the peaks recited above having very strong and strong relative intensity (e.g. peaks at 8.0 and 19.6). In some embodiments mesotrione Form 3 have an X-ray powder diffraction comprising at least the peaks recited above having very strong, strong, and medium relative intensity (e.g. at 8.0, 15.0, 18.4, 19.6, and 27.9). According to certain embodiments mesotrione Form 3 have an X-ray powder diffraction comprising at least the peaks recited above having very strong, strong, and medium relative intensity (e.g. at 8.0, 15.0, 18.4, 19.6, 20.8, 22.6, 23.9, and 27.4,and 27.9).

According to some embodiment the X-ray powder diffraction is further characterized by at least one of the following reflections quoted below as interplanar spacing d or as 2θ values:

| | |
|---|---|
| d = 6.97 Å | 2θ = 12.7 ± 0.20° |
| d = 5.89 Å | 2θ = 15.0 ± 0.20° |
| d = 4.83 Å | 2θ = 18.4 ± 0.20° |
| d = 4.52 Å | 2θ = 19.6 ± 0.20° |
| d = 4.28 Å | 2θ = 20.8 ± 0.20° |
| d = 3.93 Å | 2θ = 22.6 ± 0.20° |
| d = 3.73 Å | 2θ = 23.9 ± 0.20° |

-continued

| | |
|---|---|
| d = 3.25 Å | 2θ = 27.4 ± 0.20° |
| d = 3.20 Å | 2θ = 27.9 ± 0.20° |

The d values may deviate as much as ±1% of the indicated d values.

In some embodiments, the mesotrione Form 3 is characterized in that it has at least two of these 2θ values or d values.

In some embodiments, the mesotrione Form 3 is characterized in that it has at least three of these 2θ values or d values.

In some embodiments, the mesotrione Form 3 is characterized in that it has at least four of these 2θ values or d values.

In some embodiments, the mesotrione Form 3 is characterized in that it has at least five of these 2θ values or d values.

In some embodiments, the mesotrione Form 3 is characterized in that it has at least six of these 2θ values or d values.

In some embodiments, the mesotrione Form 3 is characterized in that it has at least seven of these 2θ values or d values.

In some embodiments, the mesotrione Form 3 is characterized in that it has at least eight of these 2θ values or d values.

In some embodiments, the mesotrione Form 3 is characterized in that it has at least nine of these 2θ values or d values.

According to some embodiments the infrared absorption spectrum is further characterized by having at least one additional peak selected from the following values expressed as $cm^{-1}$ ($\pm 1\ cm^{-1}$) at: 814, 851, 1061, 1169, 1189, 1358, 1407, 1534, and 1675.

According to some embodiments the infrared absorption spectrum is further characterized by having at least two additional peak values, at least three additional peak values, at least four additional peak values, at least five additional peak values, at least six additional peak values, at least seven additional peak values, at least eight additional peak values, or all nine additional peak values, selected from the values recited above.

In some embodiments a solid form of mesotrione has a phase purity of at least about 5% Form 3 mesotrione.

In some embodiments a solid form of mesotrione has a phase purity of at least about 10% Form 3 mesotrione.

In some embodiments a solid form of mesotrione has a phase purity of at least about 25% Form 3 mesotrione.

In some embodiments a solid form of mesotrione has a phase purity of at least about 50% Form 3 mesotrione.

In some embodiments a solid form of mesotrione has a phase purity of at least about 75% Form 3 mesotrione.

In some embodiments a solid form of mesotrione has a phase purity of at least about 80% Form 3 mesotrione.

In some embodiments a solid form of mesotrione has a phase purity of at least about 85% Form 3 mesotrione.

In some embodiments a solid form of mesotrione has a phase purity of at least about 90% Form 3 mesotrione.

The term "phase purity" means the solid state purity of mesotrione with regard to a particular crystalline or other form of the mesotrione as determined by one or more of the analytical methods e.g. described herein.

The percentage (%) values of the phase purity refer to w/w (weight %).

In some embodiments the solid form of mesotrione is a substantially phase pure form of mesotrione Form 3.

As used herein, the term "substantially phase pure form" or "substantially pure", when used in reference to mesotrione Form 3, refers to mesotrione Form 3 which is equal or greater than about 80 weight % pure. This means that the mesotrione Form 3 does not contain more than about 20 weight % of any other compound and, in particular, does not contain more than about 20 weight % of any other form of mesotrione. Preferably, the term "substantially pure", when used in reference to mesotrione Form 3, refers to mesotrione Form 3 which is equal or greater than about 85 weight % pure. This means that the mesotrione Form 3 does not contain more than about 15 weight % of any other compound and, in particular, does not contain more than about 15 weight % of any other form of mesotrione. More preferably, the term "substantially pure", when used in reference to mesotrione Form 3, refers to mesotrione Form 3 which is equal or greater than about 90 weight % pure. This means that the mesotrione Form 3 does not contain more than about 10 weight % of any other compound and, in particular, does not contain more than about 10 weight % of any other form of mesotrione.

Even more preferably, the term "substantially pure", when used in reference to mesotrione Form 3, refers to mesotrione Form 3 which is equal or greater than about 95 weight % pure. This means that the mesotrione Form 3 does not contain more than about 5 weight % of any other compound and, in particular, does not contain more than about 5 weight % of any other form of mesotrione. Even more preferably, the term "substantially pure", when used in reference to mesotrione Form 3, refers to mesotrione Form 3 which is equal or greater than about 97 weight % pure. This means that the mesotrione Form 3 does not contain more than about 3 weight % of any other compound and, in particular, does not contain more than about 3 weight % of any other form of mesotrione.

In specific embodiments the term "substantially pure" includes a form of mesotrione that is equal or greater than about 98 weight %, 99 weight %, 99.5 weight %, or 99.8 weight % pure and also including equal to about 100 weight % pure.

According to a specific embodiment the polymorph Form 3 exhibits an infrared spectrum substantially as shown in FIG. 1.

According to a specific embodiment the polymorph Form 3 exhibits an X-ray powder diffraction pattern substantially as shown in FIG. 3.

According to a specific embodiment the polymorph Form 3 exhibits a $^{13}C$ NMR spectrum substantially as shown in FIG. 5.

According to some embodiments mesotrione Form 3 may be used in a mixture with other mesotrione forms (e.g. mesotrione Form 1, mesotrione Form 2, and a mixture thereof).

One of skill in the art will appreciate that the peak positions (2θ) will show some inter-apparatus variability, typically as much as ±0.2°. Accordingly, where polymorphic forms are described by characteristic X-ray powder diffraction peaks, the peak positions (2θ) should be understood as encompassing such variability. Similarly, where the solid forms of the present invention are described as having an X-ray powder diffraction pattern substantially as that shown in a given figure, the term "substantially as shown" is intended to encompass such inter-apparatus variability in diffraction peak positions. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

Similarly, FT-IR spectra may show variability as much as $\pm 1\ cm^{-1}$. $^{13}C$ NMR spectra may show variability as much as ±0.1 ppm.

According to another aspect of the invention there is provided a process for the preparation of a crystalline polymorph Form 3 of 2-[4-(methylsulfonyl)-2-nitrobenzoyl]-1,3-cyclohexanedione as described in the invention, comprising:

(a) crystallizing Form 3 from an aqueous solution comprising (i) an ammonium salt of 2-[4-(methylsulfonyl)-2-nitrobenzoyl]-1,3-cyclohexanedione and (ii) a polar aprotic solvent selected from dimethylsulfoxide (DMSO), N-methyl-2-pyrrolidone (NMP), dimethylformamide (DMF), and mixtures of said solvents, by acidification of said solution; and (b) isolating the resulting precipitate of Form 3.

According to a preferred embodiment the polar aprotic solvent is dimethylsulfoxide (DMSO).

In some embodiments the polar aprotic solvent comprises at least DMSO.

In some embodiments the solvent is a mixture of (i) DMSO; and (ii) NMP and/or DMF.

According to an embodiment of the invention the crystallization is performed at a pH below 6.

According to a preferred embodiment the pH is in the range 4.5-4.8.

Referring to step (a) in the process, according to a specific embodiment the volume ratio of said polar aprotic solvent to water in said aqueous solution is in the range 4:96 to 20:80 v:v (volume:volume) polar aprotic solvent:water. According to a more specific embodiment the volume ratio of said aprotic solvent to water is in the range 5:95 to 15:85 v:v polar aprotic solvent:water. According to even more specific embodiment the volume ratio of said polar aprotic solvent to water is in the range 8:92 to 12:88 v:v polar aprotic solvent:water.

According to a specific embodiment, the process comprising:

(a) preparing an aqueous solution including (i) mesotrione ammonium salt; and (ii) a polar aprotic solvent selected from dimethylsulfoxide (DMSO), N-methyl-2-pyrrolidone (NMP), dimethylformamide (DMF), and mixtures of said solvents;

(b) effecting crystallization of mesotrione from the solution by acidification of said solution; and (c) isolating the resulting precipitate of Form 3.

According to a specific embodiment, mesotrione ammonium salt is prepared by dissolving mesotrione being different than Form 3 in an aqueous solution by an addition of an ammonium base.

In a specific embodiment the ammonium base is $NH_4OH$.

The addition of the ammonium base leads to an ammonium salt of mesotrione being formed, having high solubility. Preferably, mesotrione is being fully solubilized and no mesotrione remains out of solution.

In certain embodiments the pH of the mesotrione aqueous solution is increased to a pH of about 9.5-12, preferably about 10-11, and more preferably about 10.5-11 by the addition of an ammonium base to form a mesotrione ammonium salt.

In some embodiments said effecting crystallization of mesotrione from the solution is conducted by adjusting the pH to a value below 6.

According to a preferred embodiment the pH is adjusted to the range 4.5-4.8.

In a specific embodiment the mesotrione Form 3 is obtainable by the process described in the invention.

Mesotrione Form 3 crystals crystallize in a form of larger crystals as compared for example to Form 2 which is advantageous as they can be conveniently filtered at the manufacturing plant and therefore easily handled.

According to some embodiments the particle size of Form 3 are characterized by having a d(0.1) in the range 7-10 micrometer (micron).

As used herein the term "d(0.1)=7-10 micrometer" or "d10=7-10 micrometer", indicates that 10% by volume of the particles size (in diameter) is less than or equal to a value in the range 7-10 micrometer.

The d(0.1) may be for example 7, 7.5, 8, 8.5, 9, 10 micrometer. The d(0.1) may be for example any intermediate range between the above indicated values.

Particle size measurements are typically conducted by a method such as laser diffraction.

Particle size measurements can be conducted on Malvern Mastersizer 2000 instrument, using a laser diffraction method.

In some embodiments, the process for preparation of mesotrione Form 3 is carried out in presence of crystals of mesotrione Form 3 as described in the invention.

Thus, mesotrione Form 3 may be also prepared by seeding an aqueous solution comprising a dissolved mesotrione (e.g. by preparing a salt of mesotrione such as a sodium or an ammonium salt) with crystals of mesotrione Form 3 as described in the invention, wherein mesotrione Form 3 is ultimately obtained.

Thus for example mesotrione Form 3 may be selectively obtained using the process as described for example in WO2007/083242 incorporated herein by reference in its entirety, using mesotrione Form 3 as seed crystals instead of mesotrione Form 1.

The process for obtaining mesotrione Form 3 may include: selectively controlling the crystallization of the Form 3 polymorph of mesotrione from an aqueous mesotrione solution, the process comprising using a semi-continuous or continuous crystallization process, wherein the aqueous mesotrione solution is introduced to a crystallizer containing seed crystals predominantly of Form 3 in a semi-continuous or continuous manner, and wherein said Form 3 mesotrione is ultimately obtained.

In some embodiments the pH of the mesotrione solution is increased to a pH of >9 (above 9), preferably prior to addition to the crystallizer.

In some embodiments the mesotrione solution is added to the crystallizer while maintaining the pH in the crystallizer at 4.0-6.0, more preferable 4.5-4.8.

In some embodiments the pH in the crystallizer is maintained by the addition of acid to the mesotrione solution.

The process for converting Form 1 or 2 mesotrione to Form 3 mesotrione, may comprise introducing a mesotrione salt solution, obtained by dissolving Form 1 or 2 mesotrione in an alkaline aqueous medium, to a crystallizer containing seed crystals predominantly of Form 3 in a semi-continuous or continuous manner and wherein said Form 3 mesotrione is ultimately obtained.

In some embodiments the pH of the solution of Form 1 or 2 mesotrione is increased to a pH of >9, preferably prior to addition to the crystallizer.

In some embodiments the pH in the crystallizer is maintained by the addition of acid to the mesotrione solution.

Form 1 mesotrione may be obtained for example from Syngenta Crop Protection, United States, under the trade name Callisto.

Form 2 may be prepared for example according to the process described in WO 2006/021743.

Mesotrione Form 3 may be used in the form of herbicidal compositions i.e. in association with compatible diluents or carriers suitable for use in herbicidal compositions.

Thus, according to a further aspect of the invention there is provided a herbicidal composition comprising a crystalline polymorph Form 3 of 2-[4-(methylsulfonyl)-2-nitrobenzoyl]-1,3-cyclohexanedione as described in the invention; and an herbicidally acceptable diluent or carrier.

The diluent or carrier may be for example a liquid, a solid or a semi-solid carrier.

The term "herbicidal composition" is used herein in a broad sense, to include not only compositions which are ready for use as herbicides but also concentrates which should be diluted before use.

The term "herbicidally acceptable carrier" as used herein is intended to include any material that facilitates application of a composition of the invention to the intended subject, which may for example be a weed and/or a locus thereof, or that facilitates storage, transport or handling. Carriers used in compositions for application to weeds and/or locus thereof are preferably non-phytotoxic or only mildly phytotoxic. Most preferably the carrier is non-phytotoxic. A suitable carrier may be a solid, liquid, or semi-solid depending on the desired formulation and are well known in the art. The term "herbicidally acceptable carrier" covers also all adjuvants, e.g., inert components, dispersants, surfactants, tackifiers, binders, etc., that are ordinarily used in herbicidal formulation technology; these are well known to those skilled in herbicidal formulation.

The herbicide (mesotrione Form 3) can generally be formulated in a dosage form suitable for a purpose of use by for example dissolving or dispersing in a proper liquid or semi-solid carrier or mixing with or absorbing to a proper solid carrier.

Thus, the herbicide may be mixed with one or more solid, semi-solid, or liquid carriers and prepared by various means, e.g., by homogeneously mixing, blending and/or grinding the herbicide with suitable carriers using conventional formulation techniques. Such formulation can be further prepared as needed by adding adjuvants, for instance, emulsifiers, dispersants, spreading agents, penetrating agents, wetting agents, binders, thickeners, preservatives, antioxidants, colorants or others according to a known method.

It may be desirable to incorporate one or more surface-active agents into the compositions of the present invention. Such surface-active agents are advantageously employed in both solid, semi-solid and liquid compositions, especially those designed to be diluted with carrier before application. The surface-active agents can be anionic, cationic or nonionic in character and can be employed as emulsifying agents, wetting agents, suspending agents, or for other purposes.

Other adjuvants commonly used in agricultural compositions include for example antifoam agents, sequestering agents, neutralizing agents, buffers, dyes, odorants, spreading agents, sticking agents, dispersing agents, thickening agents, freezing point depressants, antimicrobial agents, and the like, may be used.

The compositions may also contain other compatible components, for example, other herbicides, fertilizers, plant growth regulants, fungicides, insecticides, and the like.

In practice, the herbicide may be applied as one or more formulations (compositions) containing the various adjuvants and carriers known to or used in the industry for facilitating application and efficacy. The choice of formulation and mode of application for a given compound may affect its activity, and selection will be made accordingly. The herbicide used in the invention (i.e. mesotrione Form 3) may thus be formulated as granules, as microgranule, as wettable powders, as emulsifiable concentrates, as suspension concentrate, as soluble concentrate, as powders or dusts, as flowables, as solutions, as suspensions or emulsions, as controlled release forms such as microcapsules, or others.

Suitable adjuvants or carriers should not be phytotoxic to valuable crops, particularly at the concentrations employed in applying the compositions for selective weed control in the presence of crops, and should not react chemically with the mesotrione Form 3 or other composition ingredients. Such mixtures can be designed for application directly to weeds or their locus or can be concentrates or formulations that are normally diluted with additional carriers before application.

These herbicidal composition of the present invention may comprise for example from about 0.01% to about 99% by weight, preferably from about 0.5 to about 90% by weight of the active ingredient (mesotrione Form 3), based on the total amount of the composition. The optimum amount for a given compound will depend inter alia upon the type of composition, mode of application, application equipment, and nature of the weeds to be controlled, etc.

Liquid compositions of the invention may be applied by spraying, atomizing, watering, introduction into the irrigation water, or any other suitable means for broadcasting or spreading the liquid.

According to a specific embodiment the composition is for use in weed control.

According to an additional aspect of the invention there is provided use of a crystalline polymorph Form 3 of mesotrione as described in the invention for the control of weeds.

According to a further aspect of the invention there is provided a method for weed control comprising applying to one or both the weeds and their habitat an effective amount of the crystalline polymorph Form 3 as described in the invention.

As used herein the term "weed" refers to an unwanted plant that is growing in a place or in a manner that is detrimental to a plant of interest. As used herein the term "weed control" means killing, damaging, or inhibiting the growth of the weed. In a specific embodiment the term "weed control" refers to significant damage, caused by the herbicide, to the bulk of the weeds wherein said weeds are either dead or dying, thereby not competing with crops for subsistence.

As used herein by the term "effective amount of the crystalline polymorph Form 3" is meant an amount of mesotrione Form 3 or composition comprising thereof which causes a controlling or modifying effect upon the growth of weeds. Such controlling or modifying effects include all deviations from natural development such as killing, retardation, leaf burn, bleaching, dwarfing, defoliation, stunting, and the like.

The weeds may be for example grasses or broadleaf weeds.

The method of the invention involves applying the composition to the locus of the weeds where control is desired. The term "locus" is intended to include, but not limited to, soil, seeds, and seedlings, as well as established vegetation. The application may be post-emergent application or pre-emergent application.

Thus, the method according to the invention involves applying an effective amount of the mesotrione Form 3 as described herein to an area of land comprising weeds and/or in which pre-emergent control is desired.

The application of the herbicide may be for example to weeds and/or locus thereof (such as soil) to control the germination or growth of the weed species.

The weeds may be in an area of land that also includes plants or crops. In this instance, the herbicidal composition may, depending on the crop, be applied to both the crops and weeds to take advantage of the selectivity of the mesotrione Form 3 for a plant to kill weeds without adversely effecting crops.

Preferably, when applied to a crop-growing area, the rate of application should be sufficient to control the growth of weeds without causing substantial permanent damage to the crop.

Mesotrione Form 3 can be used as a herbicide of agricultural field such as field, lawn, orchard and the like and non-agricultural field. Especially, it is suitable for herbicide in field. In a specific embodiments, weeds can be controlled without damage to crops by using the present compound in agricultural field where crops such as corn, cranberry, blueberry, flax, pearl millet, asparagus, bluegrass, ryegrass, oats, rhubrab, sorghum, sugarcane, and the like is growing.

In a specific embodiment mesotrione Form 3 is useful for selective control of weeds.

In a specific embodiment mesotrione Form 3 is useful for selective control of weeds in corn (e.g. in a field where corn is growing).

Thus, mesotrione Form 3 can selectively control weeds, while leaving other plants and crops relatively unharmed.

In a specific embodiment mesotrione Form 3 can be used as a preemergence and postemergence herbicide for control of broadleaf weeds and grass weeds in field corn, production seed corn, and corn grown for silage.

In some embodiments the weed is selected from the group consisting of: *Abutilon theophrasti, Amaranthus* spp., *Amaranthus rudis, Ambrosia artemisiifolia, Ambrosia trifida, Atriplex patula, Capsella bursa-pastoris, Chenopodium* spp., *Cirsium arvense, Datura stramonium, Fumaria officinalis, Galinsoga parviflora, Galium aparine, Helianthus annuus L., Ipomea hederacea, Kochia scoparia, Lamium purpureum, Matricaria chamomilla, Mercurialis annua, Polygonum aviculare, Polygonum convolvulus, Polygonum lapathifolium, Polygonum pensylvanicum, Polygonum persicaria, Senecio vulgaris, Sinapis arvensis, Solanum nigrum, Stellaria media, Viola arvensis, Xanthium strumarium L.*, and a combination thereof.

The amount of the herbicide used can vary within a substantial range. The optimum amount employed can be determined for the use in each case by series of tests. The rate of application of the compositions of the invention will depend on a number of factors including, the nature of the desired effect, the identity of the weeds whose growth is to be controlled, the formulations selected for use, whether the compound is to be applied for pre-emergent or post-emergent control, and other factors. It is well within an ordinary skill in the art to determine the necessary amount of the active ingredient.

As a general guide, however, an application rate of from about 50 to about 500 g a.i./ha, in a specific embodiment from about 75 to about 400 g a.i./ha, in a more specific embodiment from about 200 to about 350 g a.i./ha, may be used. In some embodiments the application rate may be from about 70 to about 250 g a.i./ha. In some embodiments the application rate may be from about 70 to about 150 g a.i./ha.

The compositions of the present invention may also be applied in any concentration and application rate that will enable it to control the growth, propagation and pre-emergence of weeds in an area of land.

As used herein the term "a.i." refers to active ingredient.

When applied to a crop-growing area, preferably the rate of application should be sufficient to control the growth of weeds without causing substantial permanent damage to the crop.

Mesotrione Form 3, according to the invention, can be applied either before or after emergence of the plants. Mesotrione Form 3 can also be incorporated into the soil before sowing.

EXAMPLES

Analytical Methods
X-ray Powder Diffraction

Phase analysis of the Mesotrione samples was performed by X-ray powder diffraction (XRD) method. The data were collected on Philips 1050/70 powder diffractometer, with a graphite monochromator on diffracted beam providing Cu—Kα radiation ($\lambda=1.541$ Å) and operating at v=40 kV, I=30 mA.

The typical θ-2θ scan range was 5-31°2θ with a step size of 0.05° and a count time of 0.5 seconds per step. Scanning speed was 6° per minute.

Samples were ground prior to measurement using an agate mortar and pestle using light pressure.

The powder obtained was then pressed onto zero-background quartz in aluminum holder. Sample width: 1.5 cm, length: 2 cm, thickness: 0.5 cm.

Samples were stored and run at room temperature.

FT-IR

Mesotrione samples were measured by a Fourier transform infrared (FT-IR) spectrophotometer ReactIR™ 1000 of Mettler Toledo Autochem (ATR method, MCT detector), equipped with diamond window. Samples for IR were held in DuraSamplIR™ sampling device. The diamond sensor had a standard focusing optic of ZnSe. Samples were prepared as potassium bromide (KBr) discs.

The powdered samples were compressed in the sampling device and were measured with resolution of 4 cm$^{-1}$ and 256 scans.

$^{13}$C NMR

All solid-state $^{13}$C NMR measurements were made at ambient temperature with a Bruker DMX-500 125.76 MHz spectrometer equipped with a BL-4 cp/mas probehead and High Power/High Performance (HPHP) 1H and X-channel preamplifiers for solids. High resolution spectra were obtained using high power proton decoupling and cross-polarization (CP) with magic angle spinning (MAS) at 5.0 kHz. The magic angle was adjusted using the Br signal of KBr by detecting the side bands as described by Frye and Maciel (Frye J. S. and Maciel G. E., *J. Mag. Res.* 1982, 48:125, incorporated herein by reference in its entirety). Magnet shimming was performed on a sample of adamantane. Approximately 100 mg of sample was packed into a 4 mm diameter zirconia rotor for each experiment. Chemical shifts were referenced to external glycine-alpha polymorph (carbonyl signal at 176.03 ppm).

Example 1

A 500 ml reactor was charged with 25 g Mesotrione (Form 1 or 2), 300 ml water and 30 ml DMSO. Ammonium hydroxide (10% solution, 35 g) was added to form the ammonium salt of the compound, effectively, increasing the pH to 10.5 and forming a clear solution. Mesotrione was then precipitated by slow addition of hydrochloric acid (5% solution, 130 g) reaching pH 4.6. The slurry obtained was filtered yielding Mesotrione Form 3 as evidenced by the XRD, IR and $^{13}$C NMR.

Example 2

A 500 ml reactor was charged with 25 g Mesotrione (Form 1 or 2) and 400 ml water. Sodium hydroxide (45% solution, 7 g) was added to form the sodium salt of the compound, effectively increasing the pH to 12.5 and forming a clear solution. Form 3 seeds crystals were added to the solution and Mesotrione was then precipitated by slow addition of hydrochloric acid (5% solution, 55 g) reaching pH 4.6. The slurry obtained was filtered yielding Mesotrione Form 3 as evidenced by the XRD, IR and C$^{13}$NMR.

Table 1 lists the 2-theta, d-spacing and the intensities of the peaks for mesotrione Form 3 as compared to mesotrione Form 1 and 2.

TABLE 1

X-ray diffraction

| Form 1 | | | Form 2 | | | Form 3 | | |
|---|---|---|---|---|---|---|---|---|
| 2Th | d(A) | I(counts) | 2Th | d(A) | I(counts) | 2Th | d(A) | I(counts) |
| 7.76 | 11.396 | 70 | 7.46 | 11.855 | 79 | 8.04 | 11.001 | 11850 |
| 8.45 | 10.465 | 466 | 8.08 | 10.945 | 43 | 10.34 | 8.557 | 295 |
| 10.44 | 8.475 | 156 | 10.28 | 8.602 | 219 | 12.71 | 6.967 | 189 |
| 11.40 | 7.763 | 324 | 11.82 | 7.486 | 337 | 14.22 | 6.230 | 423 |
| 13.05 | 6.784 | 472 | 14.14 | 6.264 | 84 | 15.05 | 5.886 | 1006 |
| 14.32 | 6.186 | 78 | 14.86 | 5.960 | 68 | 15.36 | 5.769 | 752 |
| 15.30 | 5.790 | 592 | 15.94 | 5.559 | 1625 | 15.82 | 5.602 | 727 |
| 16.03 | 5.528 | 468 | 16.50 | 5.372 | 226 | 16.13 | 5.494 | 372 |
| 16.99 | 5.219 | 1334 | 16.99 | 5.217 | 582 | 17.39 | 5.099 | 107 |
| 17.35 | 5.111 | 2000 | 17.47 | 5.077 | 113 | 18.36 | 4.833 | 537 |
| 18.66 | 4.755 | 434 | 19.00 | 4.671 | 1831 | 18.70 | 4.746 | 852 |
| 19.00 | 4.672 | 956 | 20.30 | 4.373 | 992 | 19.64 | 4.519 | 1521 |
| 19.25 | 4.611 | 546 | 20.55 | 4.322 | 1076 | 20.77 | 4.277 | 978 |
| 19.45 | 4.563 | 422 | 21.82 | 4.074 | 187 | 21.15 | 4.201 | 2017 |
| 21.05 | 4.221 | 894 | 22.48 | 3.955 | 1000 | 22.63 | 3.930 | 951 |
| 21.31 | 4.169 | 244 | 23.25 | 3.825 | 1287 | 23.88 | 3.726 | 753 |
| 22.25 | 3.996 | 580 | 23.70 | 3.754 | 477 | 24.23 | 3.673 | 748 |
| 22.95 | 3.875 | 656 | 25.09 | 3.549 | 129 | 25.06 | 3.554 | 397 |
| 23.25 | 3.825 | 460 | 25.64 | 3.474 | 90 | 25.63 | 3.475 | 503 |
| 24.20 | 3.678 | 262 | 25.99 | 3.428 | 76 | 27.07 | 3.294 | 332 |
| 24.60 | 3.619 | 1290 | 26.55 | 3.357 | 107 | 27.41 | 3.254 | 524 |
| 25.21 | 3.532 | 346 | 27.11 | 3.289 | 240 | 27.87 | 3.201 | 1040 |
| 25.63 | 3.475 | 396 | 27.53 | 3.240 | 242 | 28.45 | 3.137 | 453 |
| 25.90 | 3.440 | 188 | 28.59 | 3.123 | 580 | 29.15 | 3.063 | 190 |
| 26.65 | 3.345 | 366 | 29.53 | 3.025 | 280 | 29.91 | 2.987 | 100 |
| 27.28 | 3.269 | 404 | 30.20 | 2.959 | 302 | 30.38 | 2.942 | 293 |
| 28.34 | 3.149 | 758 | | | | 30.69 | 2.913 | 393 |
| 28.60 | 3.121 | 734 | | | | 31.19 | 2.867 | 288 |
| 29.40 | 3.038 | 174 | | | | 31.52 | 2.839 | 530 |
| 30.02 | 2.976 | 222 | | | | 32.49 | 2.756 | 244 |
| 30.91 | 2.893 | 144 | | | | 33.13 | 2.704 | 86 |
| | | | | | | 34.37 | 2.609 | 294 |
| | | | | | | 34.86 | 2.574 | 191 |

TABLE 2

$^{13}$C NMR spectra

Chemical shifts (ppm) in the cp/mas $^{13}$C NMR spectrum of Mesotrione samples; Form 1; Form 2; and Form 3, as well as those of Form 1 and 2 from the International Patent Publication No. WO2006/021743 (WO '743).

| WO '743 FORM 1 | −0.46 PPM(*) | FORM 1 SAMPLE | WO '743 FORM 2 | −0.46 PPM(*) | FORM 2 SAMPLE | FORM 3 SAMPLE |
|---|---|---|---|---|---|---|
| 196.580 | 196.12 | 196.2 | 195.275 | 194.82 | 194.6 | 196.1 |
| 195.366 | 194.91 | 195.0 | — | — | — | 192.6 |
| — | — | — | — | — | — | 192.0 |
| 145.290 | 144.83 | 144.8 | 143.499 | 143.04 | 142.9 | 145.9 |
| 142.619 | 142.16 | 142.2 | — | — | — | 142.4 |
| 141.550 | 141.09 | 141.1 | 141.566 | 141.11 | 140.9 | 140.2 |
| 134.896 | 134.44 | 134.5 | 135.534 | 135.07 | 134.9 | 132.1 |
| 128.776 | 128.32 | 128.3 | 127.860 | 127.40 | 127.3 | 130.3 |
| 122.899 | 122.44 | 122.5 | 125.917 | 125.46 | 125.3 | 119.9 |
| 113.165 | 112.71 | 112.7 | 113.386 | 112.92 | 112.8 | 113.1 |
| 43.633 | 43.17 | 43.1 | 43.639 | 43.18 | 43.1 | 42.0 |
| 39.165 | 38.71 | 38.7 | 37.228 | 36.77 | 36.7 | 36.1 |
| 33.142 | 32.68 | 32.7 | 31.886 | 31.43 | 31.2 | 30.9 |
| 19.300 | 18.84 | 18.9 | 19.937 | 19.48 | 19.4 | 19.6 |

(*)systematic correction.

It is apparent that a different compound was used as the external spectral reference standard in WO '743, since the peaks reported in the WO '743 for form 1 and 2 have a systematic mean difference of 0.46 ppm (estimated standard deviation of 0.10 ppm) farther from the 'zero' value in the spectra described herein. In the present invention we use the glycine carbonyl resonance at 176.03 ppm as a spectral reference. However the compound used as a spectral reference in WO '743 was not reported.

It is evident from the above identification methods that the Mesotrione obtained is a new distinct crystal polymorph, different from the previously known Form 1 and Form 2.

Example 3

Selectivity Pot Trials with Mesotrione 100SC Formulations

The selectivity of two Mesotrione 100SC (containing 100 g/l mesotrione) formulations was compared for two crystal modifications (1 and 3).

Methods:

Two suspension concentrate formulations of Mesotrione were prepared using the following recipe: Mesotrione 103 g, ethylene oxide propylene oxide block copolymer 33g, ethoxylated fatty acid 6 g, propylene glycol 60 g, ethoxylated castor oil (Emulsogen EL 360 [Clariant]) 220 g, Kelzan ASX (Xanthan gum) [CP Kelco, US., Inc., Atlanta, Calif., US] 1.4 g, Proxel GXL (preservative) [Arch UK Biocides Ltd.] 0.7 g, silicone antifoam 2 g, and water 634 g.

All the ingredients, except Emulsogen EL 360 and the Kelzan blend (Kelzan ASX+Proxel GXL+water) were mixed together. When homogenous they were milled in a bead mill. After milling, the Emulsogen EL 360 was mixed into the formulation followed by the Kelzan blend.

The first formulation was prepared using Mesotrione form 1 while the second was prepared using Mesotrione Form 3.

3500 ml of the suspension concentrate formulations (mesotrione 100SC) were diluted with water to a volume of 200 L.

The test was performed on three corn varieties. The corn varieties were sown in plastic pots (400 cc) filled with heavy soil. Each treatment was sprayed in 5 replicates. The trial was performed in a glasshouse with controlled temperature (20-30°).

Post emergence spraying was performed two weeks after sowing. The trials were sprayed with a mechanical sprayer, with a spray volume of 200 L/ha (equivalent to 3500 ml/ha mesotrione 100SC). The plants were irrigated 24 H (hours) after spraying. Selectivity evaluations were conducted during the trial according to the following scale:
0=Crop completely dead (necrotic).
100=Plants without any phytotoxic damage.

In the table below "control" refers to non treated corn varieties.

TABLE 3

Corn varieties and their growth stage during the spraying

| Crop variety | No. Leaves | Height cm |
|---|---|---|
| Popcorn var. 630 | 3-4 | 20-25 |
| Forage Corn var. 32p75 | 3-4 | 20-25 |
| Forage Corn var. Simon | 3-4 | 20-25 |

TABLE 4

Formulation selectivity in Forage corn 32P75

| | Rate | Forage Corn var. 32P75 Development Days After Application | | | |
|---|---|---|---|---|---|
| Treatment | ml/ha | 3 | 7 | 15 | 22 |
| Control | — | 100 | 100 | 100 | 100 |
| Mesotrione form 1 | 3500 | 50 | 85 | 95 | 100 |
| Mesotrione form 3 | 3500 | 75 | 95 | 100 | 100 |

TABLE 5

Formulation selectivity in Forage corn 'Simon'

| | Rate ml/ha | Forage Corn var. Simon Development Days After Application | | | |
|---|---|---|---|---|---|
| Treatment | | 3 | 7 | 15 | 22 |
| Control | — | 100 | 100 | 100 | 100 |
| Mesotrione form 1 | 3500 | 60 | 80 | 98 | 100 |
| Mesotrione form 3 | 3500 | 90 | 98 | 100 | 100 |

TABLE 6

Formulation selectivity in Popcorn '630'

| | Rate ml/ha | Sweet Corn var. Popcorn Development Days After Application | | | |
|---|---|---|---|---|---|
| Treatment | | 3 | 7 | 15 | 22 |
| Control | — | 100 | 100 | 100 | 100 |
| Mesotrione form 1 | 3500 | 40 | 30 | 30 | 60 |
| Mesotrione form 3 | 3500 | 75 | 85 | 98 | 100 |

In Tables 4-6, the rate 3500 ml/ha refers to the suspension concentrate (mesotrione 100SC) formulation.
Results:
The trials show that the Form 3 crystal results in a formulation exhibiting decreased phytotoxicity and therefore safer to the corn varieties tested in this trial at the rate of 3500 ml/ha (equivalent to 350g a.i./ha).

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

It is appreciated that features from different embodiments described in the invention can be combined.

It should be understood that the individual features described hereinabove can be combined in all possible combinations and sub-combinations to produce additional embodiments and aspects of the invention.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A crystalline polymorph of 2-[4-(methylsulfonyl)-2-nitrobenzoyl]-1,3-cyclohexanedione which exhibits at least one of the following properties:
    (a) an X-ray powder diffraction pattern having a characteristic peak expressed in $2\theta$ ($\pm 0.20°2\theta$) at 8.0, said peak is characterized by having the highest intensity in the diffraction pattern;
    (b) an infrared absorption spectrum having at least one characteristic peak with a value expressed as cm-1 (+/−cm-1) selected from the group consisting of 732, 770, 793, 891, 967, 1121, 1152, 1291, 1304, and 2952;
    (c) $^{13}$C solid state NMR having at least one of the following characteristics:
        (i) $^{13}$C solid state NMR chemical shifts, with reference to a value of 176.03 ppm for the carbonyl peak of glycine, having three peaks in the range 191 to 197 ppm ($\pm 0.1$ ppm);
        (ii) $^{13}$C solid state NMR, expressed as the difference between the smallest value methylene carbon chemical shift peak and the other chemical shift values, having three peaks in the range 171.4 to 177.4 ppm ($\pm 0.1$ ppm).

2. A crystalline polymorph of 2-[4-(methylsulfonyl)-2-nitrobenzoyl]-1,3-cyclohexanedione which exhibits at least one of the following properties:
    (a) an X-ray powder diffraction pattern having a characteristic peak expressed in $2\theta$ ($\pm 0.20°2\theta$) at 8.0, said peak is characterized by having the highest intensity in the diffraction pattern;
    (b) an infrared (IR) absorption spectrum having at least one characteristic peak with a value expressed as cm-1 (+/−cm-1) selected from the group consisting of 732, 770, 793, 891, 967, 1121, 1152, 1291, 1304, and 2952;
    (c) $^{13}$C solid state NMR having at least one of the following characteristics:
        (i) $^{13}$C solid state NMR chemical shifts, with reference to a value of 176.03 ppm for the carbonyl peak of glycine, having three peaks in the range 191 to 197 ppm ($\pm 0.1$ ppm), comprising at least two peaks selected from the following values 196.1, 192.6, and 192.0 ppm ($\pm 0.1$ ppm);
        (ii) $^{13}$C solid state NMR, expressed as the difference between the smallest value methylene carbon chemical shift peak and the other chemical shift values, having three peaks in the range 171.4 to 177.4 ppm ($\pm 0.1$ ppm), comprising at least two peaks selected from the following values 176.5, 173.0, and 172.4 ppm ($\pm 0.1$ ppm).

3. The crystalline polymorph of claim 1, wherein said $^{13}$C solid state NMR chemical shifts, with reference to a value of 176.03 ppm for the carbonyl peak of glycine, have at least one peak selected from 196.1, 192.6, and 192.0 ppm (±0.1 ppm).

4. The crystalline polymorph of claim 3, wherein said $^{13}$C solid state NMR chemical shifts, with reference to a value of 176.03 ppm for the carbonyl peak of glycine, have at least two peak values selected from 196.1, 192.6, and 192.0 ppm (±0.1 ppm).

5. The crystalline polymorph of claim 1, wherein said $^{13}$C solid state NMR chemical shifts, with reference to a value of 176.03 ppm for the carbonyl peak of glycine, have all three of the peak values of 196.1, 192.6, and 192.0 ppm (±0.1 ppm).

6. The crystalline polymorph of claim 1, wherein the $^{13}$C solid state NMR chemical shifts, with reference to a value of 176.03 ppm for the carbonyl peak of glycine, further characterized by having at least one additional peak expressed in ppm (±0.1 ppm), selected from the following values at 145.9, 142.4, 140.2, 132.1, 130.3, 119.9, 113.1, 42.0, 36.1, 30.9, and 19.6.

7. The crystalline polymorph of claim 1, wherein the X-ray powder diffraction pattern is further characterized by having at least one additional peak expressed in 2θ (±0.20°2θ) selected from the following values at 15.0, 19.6, and 27.9.

8. The crystalline polymorph of claim 1 wherein the X-ray powder diffraction pattern is further characterized by having at least one additional peak expressed in 2θ (±0.20°2θ) selected from the following values at 12.7 and 18.4.

9. The crystalline polymorph of claim 1, wherein the infrared absorption spectrum is further characterized by having at least one characteristic peak with a value expressed as cm-1 (+/−cm-1) selected from the group consisting of 814, 851, 1061, 1169, 1189, 1358, 1407, 1534, and 1675.

10. The crystalline polymorph according to claim 1, wherein the polymorph exhibits an X-ray powder diffraction pattern as shown in FIG. 3.

11. The crystalline polymorph according to claim 1, wherein the polymorph exhibits an infrared spectrum as shown in FIG. 1.

12. The crystalline polymorph according to claim 1, wherein the polymorph exhibits a $^{13}$C NMR spectrum as shown in FIG. 5.

13. A process for the preparation of a crystalline polymorph of 2-[4-(methylsulfonyl)-2-nitrobenzoyl]-1,3-cyclohexanedione according to claim 1, comprising:
   (a) crystallizing the crystalline polymorph from an aqueous solution comprising (i) an ammonium salt of 2-[4-(methylsulfonyl)-2-nitrobenzoyl]-1,3-cyclohexanedione and (ii) a polar aprotic solvent selected from dimethylsulfoxide, N-methyl-2-pyrrolidone, dimethylformamide, and mixtures of said solvents, by acidification of said solution; and
   (b) isolating the resulting precipitate of the crystalline polymorph.

14. The process of claim 13, wherein the solvent is dimethylsulfoxide.

15. The process of claim 13, wherein said crystallization is performed at a pH below 6.

16. The process of claim 15, wherein said pH is in the range 4.5-4.8.

17. A herbicidal composition comprising a solid crystalline polymorph of 2-[4-(methylsulfonyl)-2-nitrobenzoyl]-1,3-cyclohexanedione according to claim 1; and a herbicidally acceptable diluent or carrier.

18. A method for weed control comprising applying to one or both of the weeds and their habitat an effective amount of the crystalline polymorph according to claim 1.

* * * * *